US010739287B2

United States Patent
Colosimo et al.

(10) Patent No.: US 10,739,287 B2
(45) Date of Patent: Aug. 11, 2020

(54) MEASUREMENT AND MONITORING OF PHYSICAL PROPERTIES OF MATERIAL UNDER TEST (MUT) FROM A VEHICLE

(71) Applicant: TransTech Systems, Inc., Latham, NY (US)

(72) Inventors: Donald D. Colosimo, Saratoga Springs, NY (US); Sarah E. Pluta, Scotia, NY (US); John W. Hewitt, Niskayuna, NY (US)

(73) Assignee: TransTech Systems, Inc., Latham, NY (US)

( * ) Notice: Subject to any disclaimer, the term of this patent is extended or adjusted under 35 U.S.C. 154(b) by 398 days.

(21) Appl. No.: 15/541,874

(22) PCT Filed: Jan. 14, 2016

(86) PCT No.: PCT/US2016/013361
§ 371 (c)(1),
(2) Date: Jul. 6, 2017

(87) PCT Pub. No.: WO2016/115318
PCT Pub. Date: Jul. 21, 2016

(65) Prior Publication Data
US 2018/0011039 A1  Jan. 11, 2018

Related U.S. Application Data

(60) Provisional application No. 62/103,835, filed on Jan. 15, 2015.

(51) Int. Cl.
*G01N 27/02* (2006.01)
*G01N 33/42* (2006.01)
*E01C 19/26* (2006.01)

(52) U.S. Cl.
CPC ......... *G01N 27/026* (2013.01); *E01C 19/264* (2013.01); *G01N 33/42* (2013.01)

(58) Field of Classification Search
CPC ........ G01N 9/24; G01N 27/02; G01N 27/026; G01N 27/22; G01N 33/42; E01C 19/264; E01C 19/266; G01R 27/26
See application file for complete search history.

(56) References Cited

U.S. PATENT DOCUMENTS 5,619,193 A * 4/1997 Doherty .............. B60R 16/0237
340/580
5,952,561 A * 9/1999 Jaselskis ............... E01C 19/288
73/78

(Continued)

FOREIGN PATENT DOCUMENTS

| EP | 2717042 A1 | 9/2014 |
| JP | H03046552 | 2/1991 |
| WO | 2014153263 A1 | 9/2014 |

OTHER PUBLICATIONS

EP Search Report for EP Application No. 16737863.7, dated Nov. 27, 2017, 16 pages.

(Continued)

*Primary Examiner* — Huy Q Phan
*Assistant Examiner* — Dustin R Dickinson
(74) *Attorney, Agent, or Firm* — Hoffman Warnick LLC

(57) ABSTRACT

Systems and methods for measuring and monitoring physical properties of a material under test (MUT) from a vehicle, e.g., using complex electromagnetic impedance. Various embodiments include a method including: obtaining displacement data about a position of a sensor array relative to a material under test (MUT); comparing the displacement data with reference displacement data to determine whether the sensor array is at a reference distance relative to the MUT; in response to determining that the sensor array is (Continued)

located at the reference distance, instructing the sensor array to transmit a set of electromagnetic impedance signals into the MUT; obtaining a return electromagnetic impedance signal from the MUT; and calculating at least one physical property of the MUT based upon the transmitted set of electromagnetic impedance signals, the return electromagnetic impedance signals, and the displacement data.

17 Claims, 39 Drawing Sheets

(56) References Cited

U.S. PATENT DOCUMENTS

| | | | |
|---|---|---|---|
| 6,119,526 | A | 9/2000 | Reigstad et al. |
| 6,188,218 | B1 | 2/2001 | Goldfine et al. |
| 6,977,597 | B2 | 12/2005 | Doherty |
| 8,547,110 | B2 | 10/2013 | Kesil et al. |
| 2002/0175691 | A1 | 11/2002 | Sovik et al. |
| 2003/0193429 | A1 | 10/2003 | Campana et al. |
| 2004/0095135 | A1 | 5/2004 | Nejikovsky et al. |
| 2004/0250612 | A1 | 12/2004 | Stridiron et al. |
| 2005/0267700 | A1* | 12/2005 | Gamache ............. G01N 27/028 702/65 |
| 2007/0046289 | A1 | 3/2007 | Troxler |
| 2008/0186205 | A1 | 8/2008 | Breed |
| 2012/0126803 | A1 | 5/2012 | Goldfine et al. |
| 2012/0245873 | A1 | 9/2012 | Donnangelo et al. |
| 2012/0263531 | A1* | 10/2012 | Rutz ....................... E01C 19/23 404/72 |
| 2013/0307564 | A1 | 11/2013 | Colosimo et al. |
| 2014/0007658 | A1 | 1/2014 | Newman |
| 2014/0278300 | A1 | 9/2014 | Lipowitz |
| 2015/0268218 | A1* | 9/2015 | Troxler ............... G01S 13/0209 342/21 |

OTHER PUBLICATIONS

Gilbert, "Measuring Asphalt Density Using a TransTech Pavement Quality Indicator as an Alternative to a Nuclear Density Gauge," TransTech System, Inc., 8 pages.

EP Search Report for EP Application No. 16737863.7, dated Mar. 2, 2018, 17 pages.

Japan Notice of Reasons for Rejection (Office Action), for Japanese Application No. 2017-556770, dated Oct. 29, 2019, 8 pages.

* cited by examiner

Electrode Shapes

Rectangular with rounded corners

Ellipsoid

Circular

MEASUREMENT AND MONITORING OF PHYSICAL PROPERTIES OF MATERIAL UNDER TEST (MUT) FROM A VEHICLE

TECHNICAL FIELD

The invention relates to systems and methods of continuously monitoring physical properties of a Material Under Test (MUT) from a vehicle using complex electromagnetic impedance. The complex impedance is measured using a sensor array mounted on a vehicle and positioned at a measured height above the surface of the MUT. The sensor array may be mounted to the vehicle through a controllable structure to maintain a reference distance between the sensor array and the surface of the MUT. The complex impedance measurements and the measured distance between the sensor array and the surface of the MUT are used to compute physical properties of the MUT.

BACKGROUND

Hot Mix Asphalt, HMA, is a highly engineered product used in the paving of roads. For the purposes discussed herein, HMA consists of three components: 1) A bitumen mixture; 2) A stone aggregate; and 3) Air. The HMA is produced in a plant where a specified stone aggregate is mixed with a specified bitumen at temperatures up to 175 degrees Celsius (approximately 350 degrees Fahrenheit). The bitumen coats the aggregate. The mix is then sent to a paving site where the mix is spread with a paving machine (also called a paver or screed). When the HMA is first laid by the paver, its temperature may be around 135 degrees Celsius (approximately 275 degrees Fahrenheit) and contain around 15% air voids. In order for the HMA to meet design criteria, the air void content is commonly reduced to around 5%. This reduction is accomplished by rolling the HMA while it is in a temperature zone which permits it to be compacted. In some cases, the HMA is compacted using one or more types of rollers. A first type of roller is a break-down roller, or vibratory roller. FIG. 1 shows a highway grade steel drum vibratory roller according to the prior art. In some cases, this vibratory roller is the first roller used in the application process, and provides most of the compaction of the HMA. A vibratory roller conventionally has one or two steel drums with rotating weights, which vibrate the drums and create a dynamic force, adding to the dead weight of the roller, and increasing the compacting force (e.g., upon the HMA). A second type of roller conventionally used in the compaction of HMA is a rubber-tired roller, or pneumatic roller, which includes a number of rubber tires staggered to provide distributed compaction coverage. The rubber-tired roller is designed to knead the surface of the HMA and close the pores formed on the top surface of the asphalt. A third type of roller used in the compaction of HMA is a finish (or, finishing) roller, which is used last (e.g., after the vibratory and/or rubber-tired rollers) to minimize or eliminate creases formed by one of the previous rollers, leaving a smooth surface.

The quality of the paving is conventionally measured by the smoothness of the finish, as well as the density of the finished product. An under-compacted asphalt mat is permeable to air and water, which shortens the pavement life. In addition, in under-compacted asphalt, the presence of undesirable air voids may make the asphalt pavement less stable, as the number of inter-particle contact points is reduced and are more susceptible to freeze-thaw conditions. On the other hand, unnecessary over-compaction may crush the aggregate asphalt, leading to a reduction of air void content, which, in turn, can make the pavement susceptible to permanent deformation. If the pavement is under-compacted or over-compacted, the paving contractor may be penalized. It is therefore beneficial to achieve the desired level/range of compaction. Measurement of density may be accomplished during or after the rolling process by various hand-held instruments following corresponding ASTM International standards that provide a point measurement of density. Conventionally, after paving is completed, a core or plug about 15.25-cm (6-in) in diameter is cut from the pavement and its density is measured according to various ASTM International standards.

This approach of spot monitoring during and after rolling presents a number of problems. One issue is that very small areas of the roadway are subject to inspection. The typical commissioning authority (e.g., department of transportation or the like) requirement is to conduct one measurement on every 1,000 feet of road lane paved. This very limited sample is likely not a representative sample of the overall paving project. One earlier conventional approach attempting to address the issue of continuously measuring asphalt density from a roller device is described in U.S. Pat. No. 5,952,561 (which is hereby incorporated by reference in its entirety). This approach was supported by the US Department of Transportation (US DOT) Research Board's Innovations Deserving Exploratory Analysis (IDEA) program in 1997. The approach described in U.S. Pat. No. 5,952,561 was based on using microwave sensors mounted in the front and back of the roller device to detect asphalt densities (see PRIOR ART, FIG. 2). The actual wave lengths recommended for detection of asphalt densities in U.S. Pat. No. 5,952,561 were in the range of 1 to 3.75-cm (30 to 8 gigahertz). However, this approach has several shortcomings. For example, it has not yet been shown that microwave sensors operating from 500 megahertz to 30 gigahertz can provide an accurate density measurement of asphalt. Further, the measurement approach described in U.S. Pat. No. 5,952,561 was based on a difference between two readings, where the error band for each reading could exceed the value of the true reading. Thus, this conventional approach proved to be impractical.

A later conventional approach was based on the continuous measurement of the change between the input vibratory loads provided by the roller and the measured response of the material under the roller. This technique is called measuring the resilient modulus, or stiffness, of the pavement. The current nomenclature for this approach is called "Intelligent Compaction", when these measurements are used to change the compactive effort delivered by the roller in a closed-loop fashion, and when combined with Global Positioning Satellites (GPS) and a Geographic Information System (GIS) mapping program.

This Intelligent Compaction approach is presented in U.S. Pat. Nos. 4,870,601, 5,727,900, 6,122,601, 6,551,019, 7,669,458, and 8,190,338 (each of which is hereby incorporated by reference in its entirety). This later conventional concept is illustrated in the prior art depiction of FIG. 3. In this approach, a vibratory impulse is imparted by the drum (or drums) of the roller into the asphalt, sub-base below the asphalt, and subgrade below the sub-base. This conventional approach assumes that the entire system can be modeled by a force being imposed on the various layers of materials, represented by a combination of springs and dampers. In the illustration in FIG. 3, there are three layers: the asphalt; the sub-base; and the sub-grade. The asphalt (or, pavement) layer is typically 25 to 30 cm (10 to 12 inches) thick, and the sub-base may have a similar thickness. The sub-base is typically an engineering specified grade of crushed rock. The sub-grade is typically the local soil that has been graded and compacted to provide the base for the road. Unlike the simplified illustration in FIG. 3, where there is a single layer of asphalt, in practice, there are multiple layers of asphalt. Within the asphalt, there is typically a base layer with a compacted thickness of about 13 cm (5.25-in), an intermediate layer with a compacted thickness of 9 cm (3.5-in) and a top or finish layer with a compacted thickness of 4.5 cm (1.75-in). The illustration in FIG. 3 is intended merely to depict paving of the base layer. As the number of asphalt layers increases and become thinner, the modeling becomes more difficult to relate the response of the individual fresh asphalt layer to the response of all of the material in the zone of influence of the vibrating roller, which is conventionally estimated to be from about 1.0 to 1.2 meters deep. This is one reason why vibratory-based Intelligent Compaction has not been very successful with asphalt pavement.

Some other problems facing vibratory-based measurement of asphalt are that the stiffness of the asphalt varies with its temperature. Cold asphalt is stiffer than warm asphalt, regardless of the actual amount of compaction. Additionally, the measurement is based on the roller drum which is around 220 cm (87-in) wide. This width of the roller may allow the roller to "bridge" over asphalt that is not being compacted.

A problem facing vibratory Intelligent Compaction is that there is presently no accepted way to convert the measured asphalt resilient modulus or stiffness into density. The actual density of the compacted asphalt is the parameter upon which engineering specifications are based.

As noted herein, the conventional approaches fail to provide a continuous quantitative determination of the density of the asphalt while it is being rolled.

The use of electromagnetic impedance measurement devices has been identified in U.S. Pat. Nos. 5,900,736, 6,414,497, and 7,219,024 (each of which is hereby incorporated by reference in its entirety) to provide a quantitative reading of the density of asphalt and other materials. However, the approaches disclosed in those patents require that the sensor remain in contact with the asphalt. In order to overcome this limitation, later approaches (as described in U.S. Pat. Nos. 7,226,239 and 7,575,395, each of which is hereby incorporated by reference in its entirety), were developed to use a then commercially available gauge in contact with the asphalt while mounted on a roller. This approach, however, was limiting in that it required the interruption of the normal roller operation to conduct measurements, and thus, was not continuous.

SUMMARY OF THE INVENTION

Aspects of the invention include methods, apparatus, and systems to continuously secure electromagnetic impedance characteristics related to the physical property (e.g., density) of a material under test (MUT), e.g., asphalt, soil, etc.

Embodiments include methods, which may be performed using one or more apparatuses constructed according to various embodiments. Some embodiments include an apparatus having a supporting structure mounted to a vehicle (the vehicle including a roller), where the supporting structure includes a sensor array for communicating with the MUT via non-contacting communication to continuously measure/monitor a density of the MUT. Various embodiments directed to the continuous measurement of density during rolling (e.g., rolling of a MUT, such as asphalt) include a supporting structure assembly mounted to the roller, and the sensor array assembly mounted to the supporting structure. In these embodiments, the supporting structure assembly includes: a variable positioning system, a distance measurement system, and a control system. The sensor array assembly can include: a signal generator operably connected with an array of electrodes, a signal generator for transmitting oscillating electromagnetic field signals through the array of electrodes (toward the MUT) at a range of selected frequencies; a signal detector operably connected to the array of electrodes, the array of electrodes in communication with the MUT; a signal comparator operably connected to the signal generator and the signal detector; and at least one computing device operably connected with the signal comparator. The at least one computing device is configured to determine the electromagnetic impedance characteristics related to the physical property (e.g., density) of the MUT under measurement. The at least one computing device can obtain data, e.g., from the distance measurement system or other systems associated with the supporting structure, about a position of the sensor array relative to the MUT, which may be used as a factor in calculating a density of the MUT. The at least one computing device may also include a user interface and a data store, allowing a user to control various aspects of the sensor array, display the data in various formats, store the data files, and transfer data files to another computer by various means. The data from this system may be included in a geographic information system (GIS) database and display according to conventional approaches.

An alternate embodiment can include a system for mounting on a vehicle other than a roller. The supporting structure in this alternative system may have either a fixed or variable position relative to the MUT. However, as with the various embodiments described herein, the supporting structure assembly includes a distance measurement system.

The method and the various embodiments of the electrode sensor arrays presented in this disclosure provide, among other things, improvements over conventional approaches by securing the continuous electromagnetic impedance spectrographic characteristic(s) of the MUT, which may then be correlated to physical properties of the MUT.

DETAILED DESCRIPTION

Figure 1:
FIG. 1 is an image of a prior art dual steel drum roller used for paving an asphalt road.
Figure 2:
FIG. 2 is a picture of a prior art density measurement system.
Figure 3:
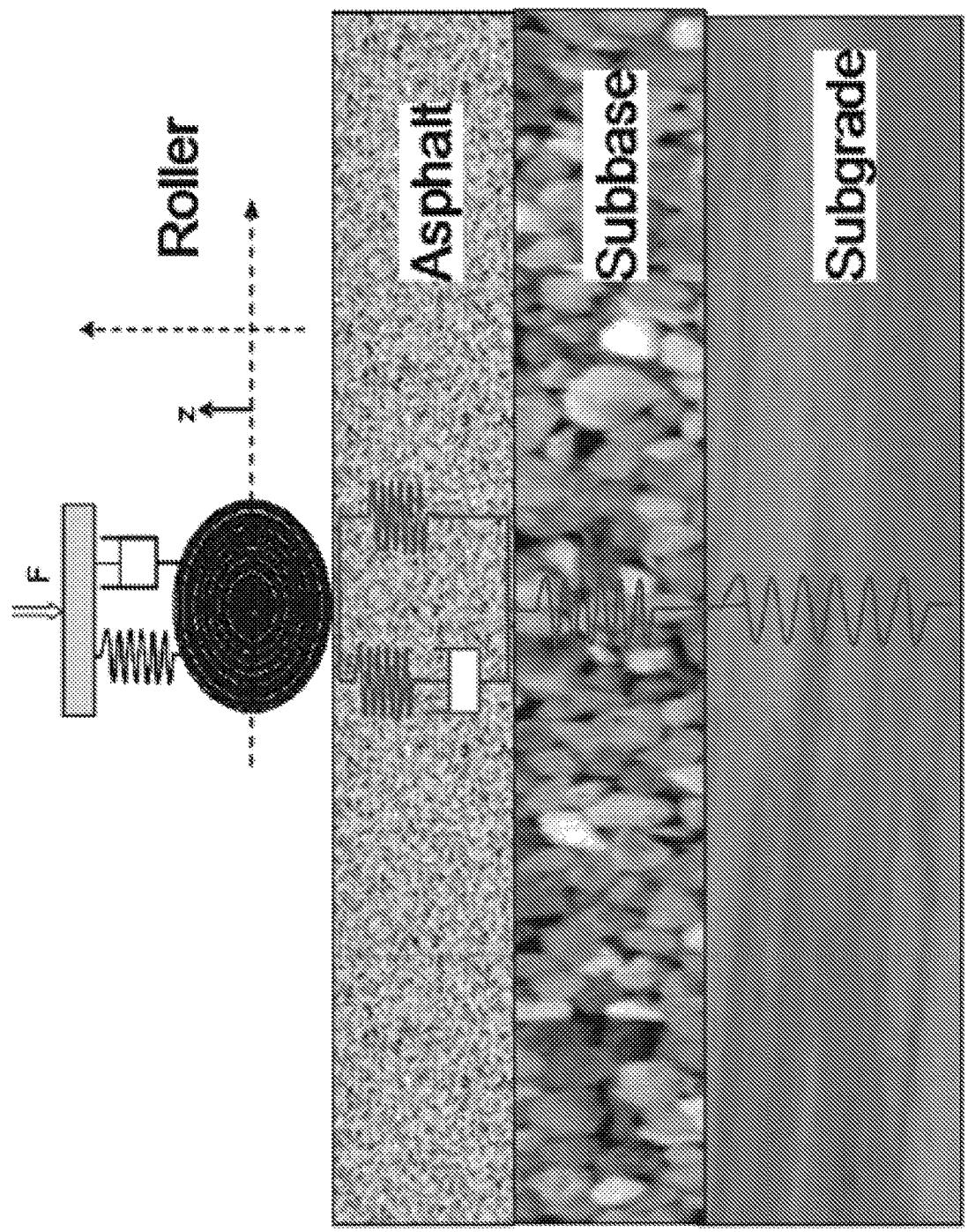
FIG. 3 is a schematic illustration demonstrating the theory of vibratory compaction to determine a resilient modulus or stiffness of asphalt according to the prior art.

The following discussion expands on and improves the methodology disclosed in prior art to provide continuous quantitative measurements of the physical property of a material under test (MUT). In the various embodiments herein, the physical property discussed is density, and the MUT is asphalt. It is understood, however, that various embodiments include approaches which can be applied to distinct physical properties and distinct MUTs. The application considered includes in-process quality control (such as for asphalt during a paving process). In some cases, the approaches, including systems and methods, can be applied during the rolling process, and in other cases, may be performed after rolling. In any case, the approaches described herein can provide for enhanced quality inspection of materials (e.g., asphalt in roads).

As noted herein, in order to obtain continuous readings of a physical property (e.g., density) of a MUT (e.g., asphalt), the inventors have discovered that the sensor for obtaining those readings should be operable while not in contact with the MUT (e.g., asphalt). In various embodiments, the inventors have utilized one or more linear electromagnetic sensor arrays similar to those described and shown in US Patent Publication 2013/0307564 and US Patent Application Nos. 61/703,488, 61/906,664, and 61/932,400 (each of which is hereby incorporated by reference in its entirety).

As described herein, various embodiments include approaches for continuously securing electromagnetic impedance data about a measured volume of a MUT (e.g., asphalt), and determining a physical property of the MUT (e.g., density) based upon that electromagnetic impedance data. In the case of a rolled MUT, e.g., asphalt, the continuous measurements/monitoring may be made as a quality control measure during the rolling process, as a quality assurance inspection after the rolling process, or as a characterization of an existing road to determine requirements for restoration.

As used herein, a material under test (MUT) can include any material, in addition to hot mix asphalt, that is capable of being characterized via one or more approaches shown and/or described herein (e.g., electromagnetic spectroscopy). In various embodiments, a MUT includes any material which may be monitored by a non-contacting electromagnetic sensor mounted on any type of vehicle with a means to control or fix the height of the sensor above the MUT.

Various embodiments described herein focus on the application of a non-contacting electromagnetic array, e.g., mounted on a paving roller, to measure the density of a MUT (e.g., asphalt) during the paving process. The vehicle on which the electromagnetic sensor is mounted may be any type of motorized or non-motorized vehicle, which provides a means to control and/or fix the height of the sensor relative to (above) the MUT. The vehicle(s) can include vehicles used in asphalt paving (e.g., rollers, and pavers), motorized vehicles (e.g., conventional motorway-traversing vehicles and non-motorway-traversing vehicles), and non-motorized vehicles (e.g., hand carts). As noted herein, the MUT may be any material that may be measured by a non-contacting electromagnetic sensor mounted on a vehicle, e.g., one or more layers of asphalt, one or more layers of sub-base, and/or one or more layers of sub-grade. The physical property or properties measured may include any physical property of the MUT that can be determined by the application of electromagnetic spectroscopy, including but not limited to density and moisture content. It is understood that the teachings described according to the various embodiments herein can be applied to any combination of a non-contacting electromagnetic sensor mounted on vehicle to measure a physical property of an MUT as described herein, as well as other approaches of the various embodiments.

In this disclosure, the electromagnetic sensor array can include a transmitting electrode and a receiving electrode. The sensor array may include any number of electrodes configured to sample various depths into the MUT and/or to obtain adequate sensitivity in securing the desired measurement of the MUT.

In the following description, reference is made to the accompanying drawings that form a part thereof, and in which is shown by way of illustration specific example embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely illustrative.

Illustrations with respect to one or more implementations, alterations and/or modifications can be made to the illustrated examples without departing from the spirit and scope of the appended claims. In addition, while a particular feature may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

Notwithstanding that the numerical ranges and parameters setting forth the broad scope of embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g., −1, −2, −3, −10, −20, −30, etc.

U.S. Pat. Nos. 5,900,736; 6,400,161; 6,414,497; and 6,677,763 (each of which is hereby incorporated by reference in its entirety) present a concentric two-electrode sensor array as a means to evaluate the density of asphalt using electromagnetic impedance characteristics of the asphalt. These approaches do not use spectrographic or tomographic approaches, but illustrates two-electrode geometries for use with electromagnetic impedance measuring devices. U.S. Pat. No. 7,219,021 (hereby incorporated by reference in its entirety) presents the use of electromagnetic impedance spectroscopy to evaluate the density and moisture of soils, with an electrode geometry similar to that in the devices shown in U.S. Pat. Nos. 5,900,736 and 6,414,497. These electrode arrays are in non-conductive communication (not electrically or physically contacting) with the MUT. US Patent Publication 2013/0307564 and U.S. Provisional Patent Application No. 61/703,488 (each of which is hereby incorporated by reference in its entirety) present two different methods of evaluating a MUT with impedance spectroscopy and impedance tomography with linear electrode arrays in conductive or non-conductive communication the MUT. U.S. Provisional Patent Application No. 61/906,664 (which is hereby incorporated by reference in its entirety), presents alternate configurations for obtaining electromagnetic tomographic and spectrographic impedance measurements from the surface of the MUT, and a process of converting those measurements into physical parameters. However, these approaches do not address the application of an array mounted on a vehicle to provide either an in-process control, an area inspection, or survey of the properties of the MUT.

Various embodiments include methods and electromagnetic sensor arrays, along with a support/control system, which controls the height of the sensor array above the MUT. In various embodiments, the electromagnetic sensor array is mounted on a vehicle to provide in-process and/or subsequent inspection or survey of selected properties of the MUT over a large area. As noted herein, such measurements may be combined with data from one or more conventional Global Positioning Satellites (GPS) systems and/or one or more Geographic Information Systems (GIS). The present disclosure presents methods, systems and computer programs to secure (e.g., continuous) electromagnetic impedance spectrographic characteristics of selected volumes of the MUT, which are used to determine physical properties, such as density, of the selected volumes of the MUT.

Figure 4:
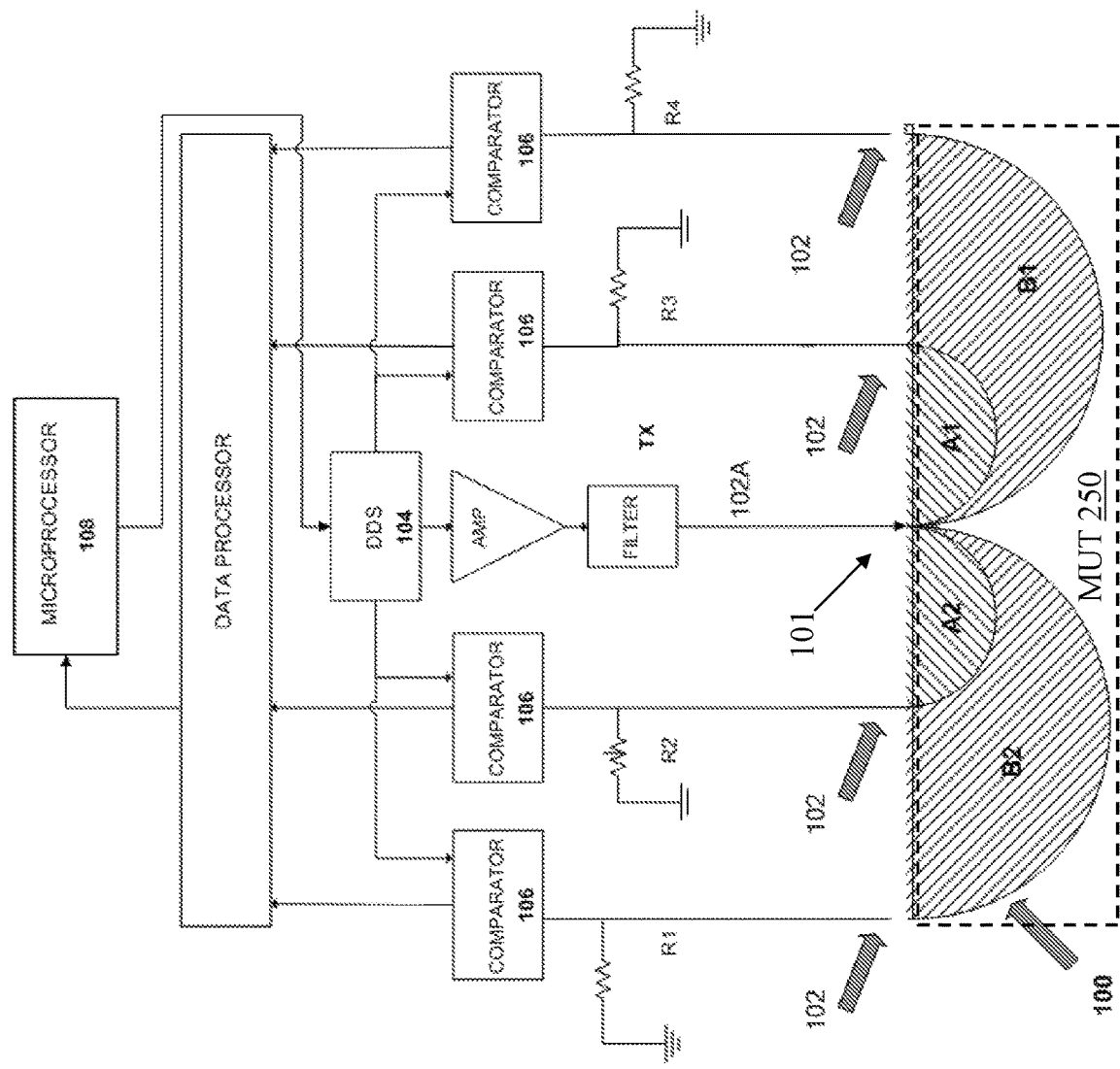
FIG. 4 is a schematic illustration of a five electrode linear array with variable functions and showing the measured volumes of the MUT.

As described in U.S. Provisional Patent Application No. 61/703,488, a schematic depiction of an impedance measuring system is shown in FIG. 4. This schematic depiction shows an impedance sensor system 100 with five electrodes 102, one of which, 102A, provides the input of the signal over a range of frequencies supplied by a signal generator 104, e.g., a DDS (Direct Digital Synthesizer). In this example, the other four electrodes can complete the circuit with the signal passing through the MUT 250. The original signal from the signal generator 104 (DDS) can be compared to the signals passing through the MUT 250. The output of the comparator 106 is the difference in the magnitude and the phase shift from the original signal to the return signal. This magnitude and phase data of the transmitted and the return signals can be communicated to the microprocessor 108 which processes the data and transmits it to a statistical process control (e.g., an embedded component in the microprocessor 108). The microprocessor 108 can also control the DDS 104 to select the frequencies to be generated. In the embodiment shown, the order of the transmitting electrode and the receiving electrodes are fixed.

In this example shown in FIG. 4, the electrodes 102 are configured to communicate with the MUT 250, but are not in electrical contact with the MUT 250, that is, they are electrically isolated from the MUT 250 (e.g., by an insulating material or an air gap). In some cases, the minimum number of electrodes in the array is two (2): a transmitting electrode and a receiving electrode. However, in other applications, the array may consist of a one-dimensional array or a two-dimensional array of multiple electrodes, e.g., 5 or more electrodes, with the electrodes operating in subsets of one transmitting electrode and one or more receiving electrodes.

In this example, the impedance characteristics of four voxels of the MUT 250 can be measured. As noted herein, a voxel is fraction of a three-dimensional space, that is, a volumetric pixel or volume element that represents a value on a regular grid in three-dimensional space. In some cases, a voxel is known as a three-dimensional equivalent of a pixel (two-dimensional element). The difference between the power of the transmitted signal and the signal passing through the MUT 250 is defined as the magnitude, m. The shift in phase between the transmitted signal and the signal passing through the MUT 250 is the phase angle, φ. These are measured by the comparators, 106, in FIG. 4. These are the measured quantities for the voxels A1, A2, B1 and B2.

In the discussion of the measurements and interpreting aspects of the complex impedance, it may be beneficial to define terms that may be calculated from the output of an electromagnetic measurement device which are the magnitude of the power difference between the transmitted signal and the signal that is transmitted through the MUT, m, and the phase angle, co, shift between the transmitted signal and the signal transmitted through the MUT. Impedance (Z) is represented mathematically as a complex relation consisting of a real part, resistance, and an imaginary part, reactance:

$$Z=R+iX;$$

Z=the complex value of Impedance;
R=m*cos φ; the Resistance;
X=m*sin φ; the Reactance;
Resistance, R, is a material's opposition to the flow of electric current;
Reactance, X, is a material's opposition to alternating current due to capacitance (capacitive reactance, $X_C$) and/or inductance (inductive reactance, $X_L$); thus, $$X=X_L+X_C,$$

which is discussed further herein.
Admittance (Y) is a complex quantity which is the inverse of Impedance, and results in the definition of the terms of Conductance and Susceptance:

$$Y=1/Z=G+iB;$$

Susceptance (B) is a complementary representation of the reactance in the term admittance and is defined mathematically as:

$$B=-X/(R^2+X^2);$$

The Susceptance may be computed from the measured properties as follows:

$$B=\text{the Susceptance}=-\sin\varphi/m;$$

The Conductance (G) may be computed from the measured properties as follows $$G=\text{the Conductance}=\cos\varphi/m.$$

In the description of the various embodiments, the value of the impedance, Z, will be used in the various equations and relations pertaining to the measurements made of the voxels in the MUT (e.g., MUT 250) and the computation of the sub-voxels. However, a value of the resistance, reactance, admittance, conductance, or susceptance may replace impedance in any of the examples below.

In addition to the above quantities to be used to develop algorithms to relate the complex impedance to a physical property of the MUT, capacitance may also be used for MUTs which do not exhibit an inductive loss. This may be typical for many MUTs of interest such as asphalt, soils, and biological materials. If there is no inductive losses, $X_L$, would be zero and, then, $X=X_C$.

Referring to the above equations, $$C=(-X/(R^2+X^2))/\omega$$

where C is capacitance;
ω is the frequency of the electromagnetic signal; and
X and R are as defined above.
The value of C may be related back to a physical property of the MUT.

It should be noted that for a tomographic solution only data at one frequency is required. However, for the use of a spectrographic analysis to characterize a property of the MUT, computations over a range of frequencies may be required. That is, the above equations are applied to data from each frequency to obtain the impedance data over the range of frequencies. These data are then applied to the Volume Differentiation and Removal methodology as described below.

Figure 5:
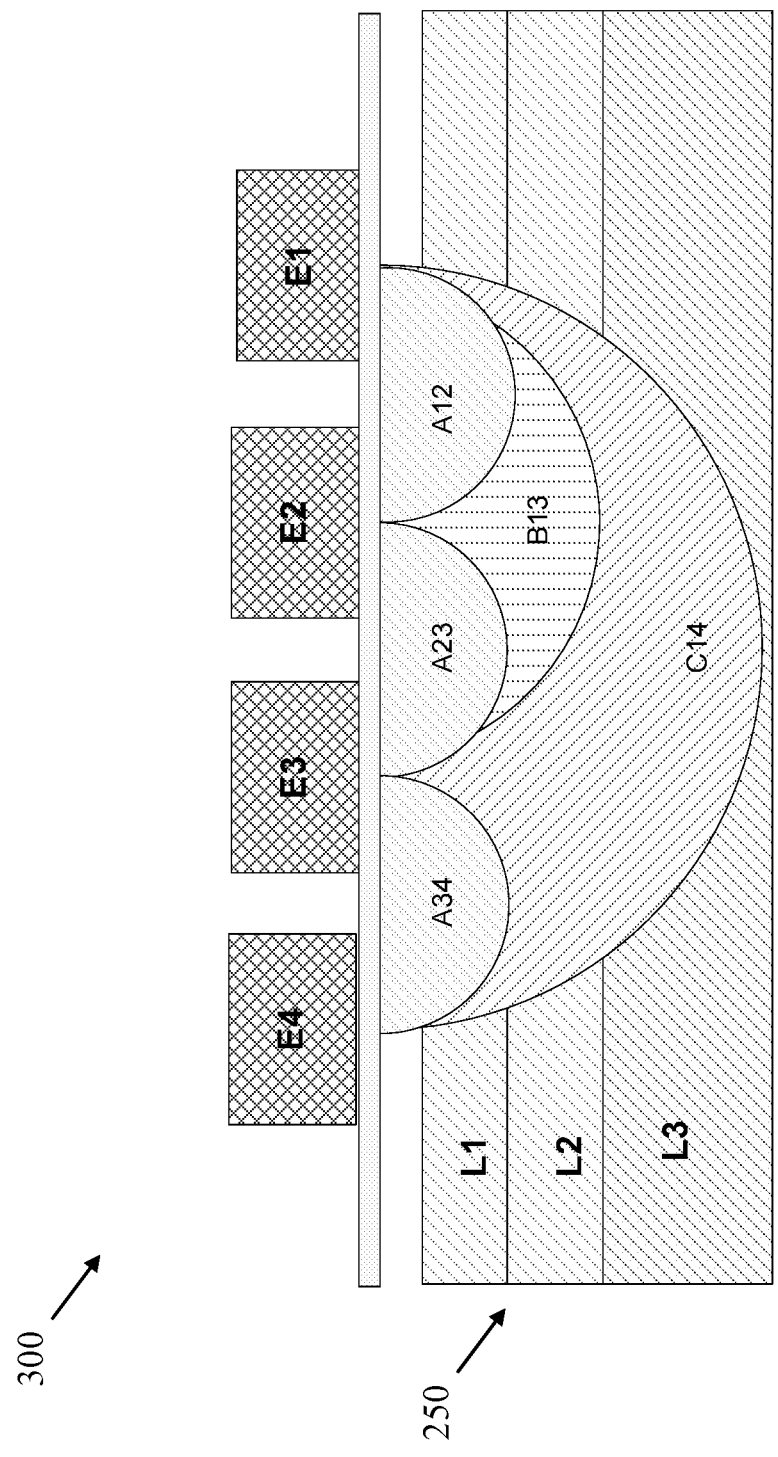
FIG. 5 is a schematic illustration of the use of a four electrode array to measure different volumes of the MUT.
Figure 6:
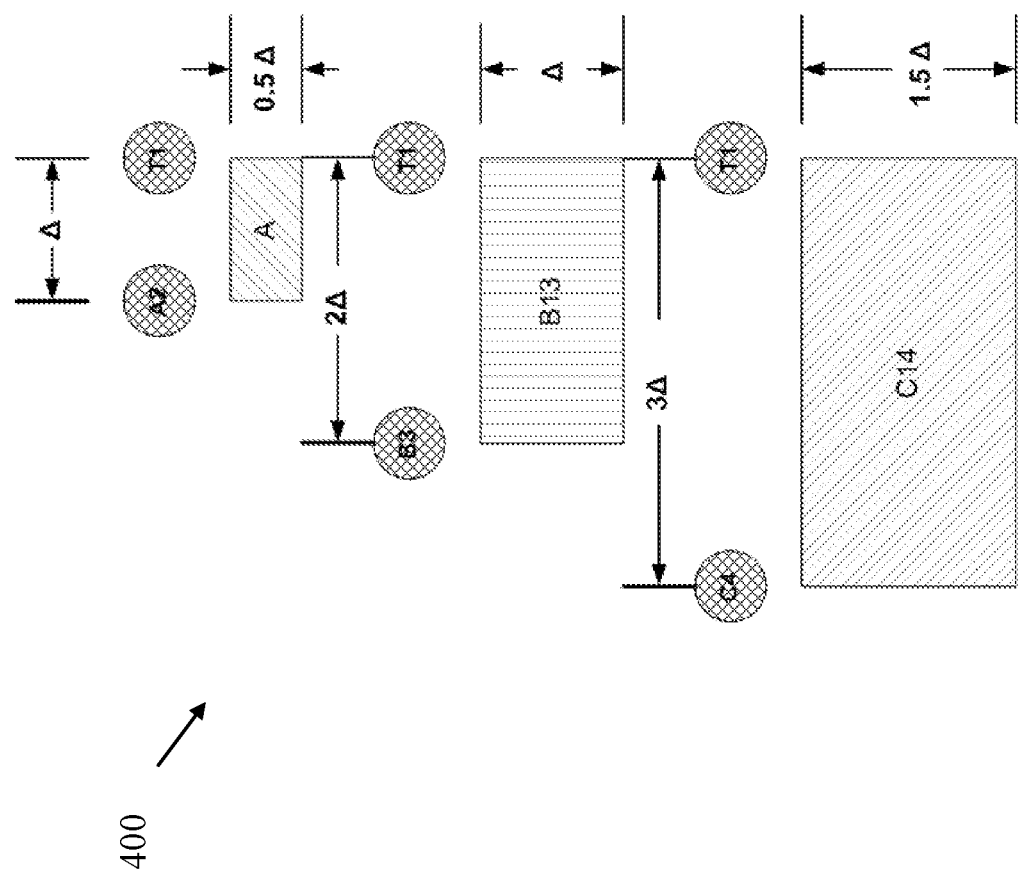
FIG. 6 is a schematic illustration of the different measured volumes of FIG. 5.
Figure 7:
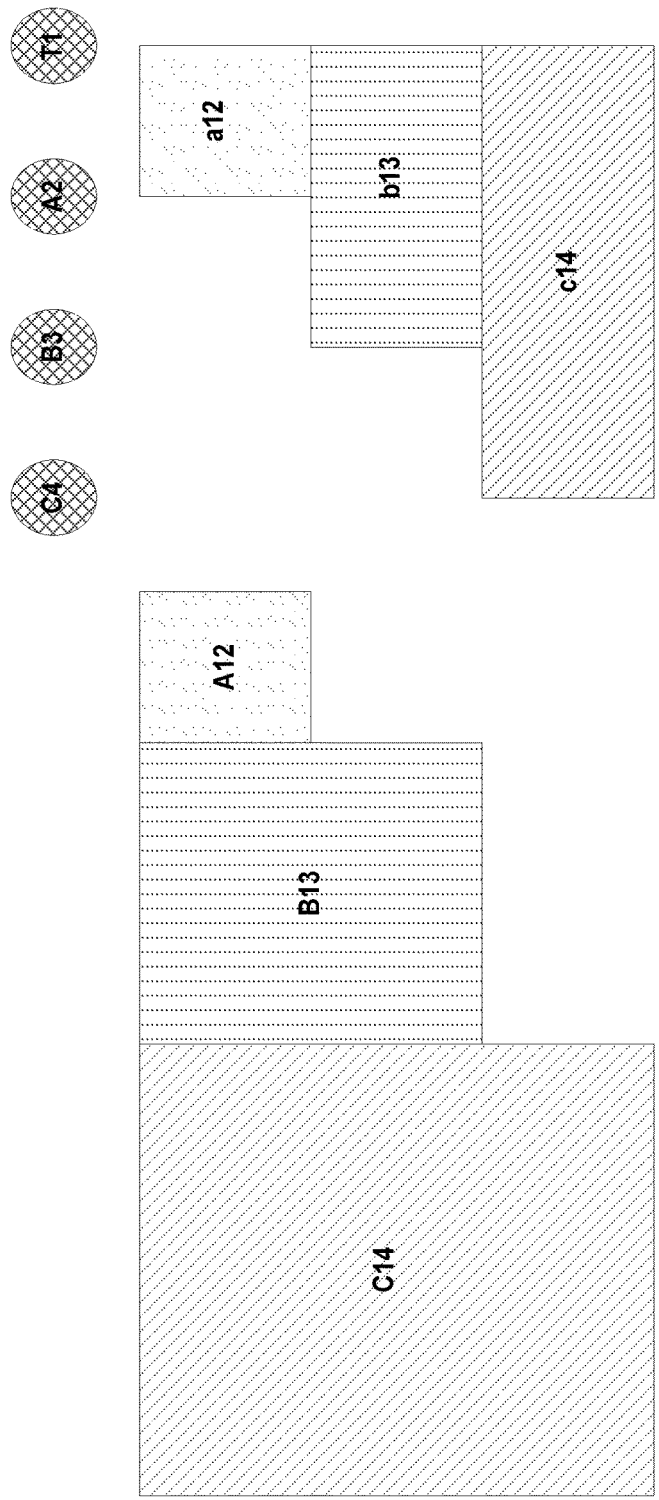
FIG. 7 is a schematic illustration of the relation of the measured volumes to the computed volumes in FIGS. 5-6.
Figure 8:
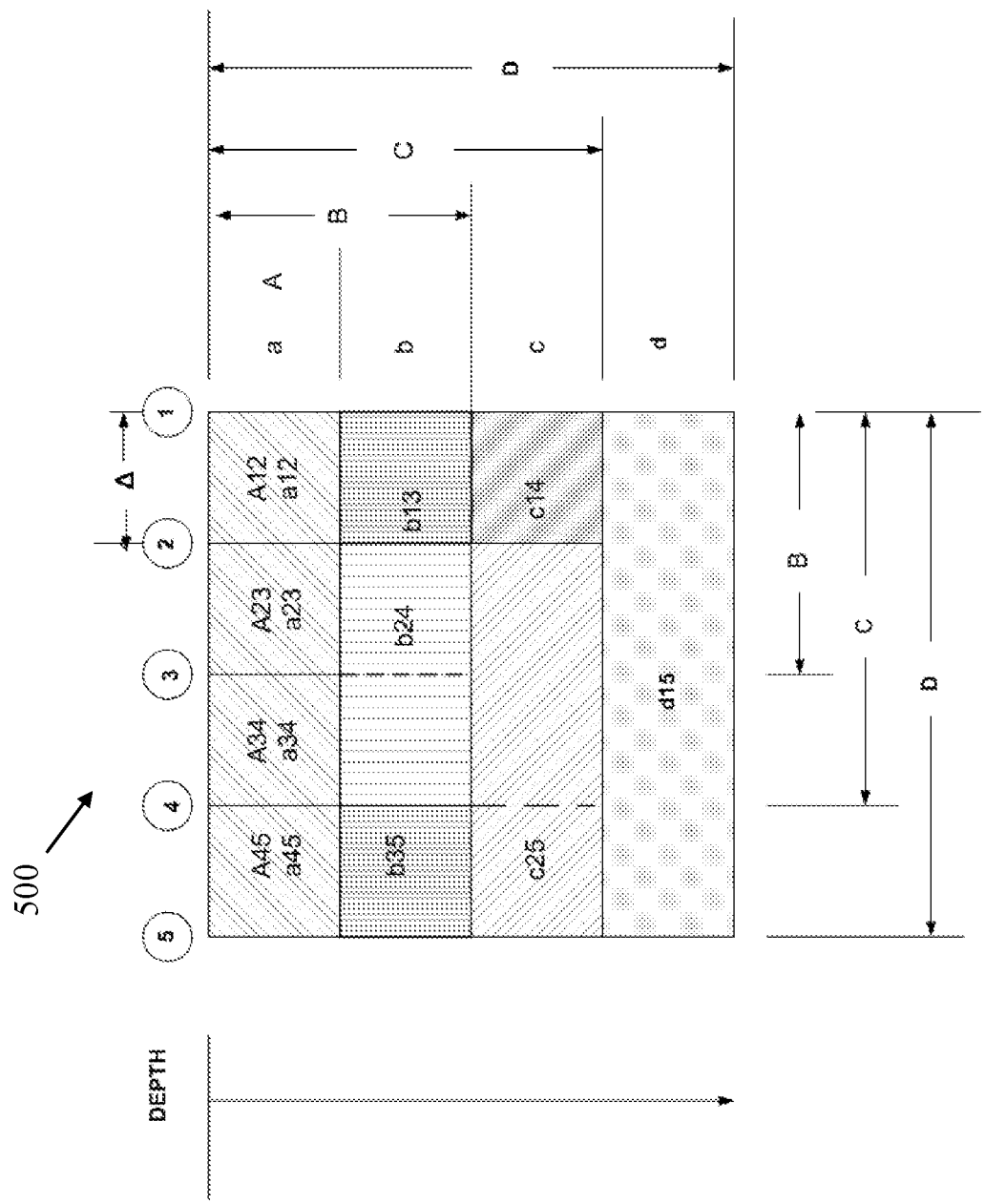
FIG. 8 is a schematic illustration of the relation of and the nomenclature for the computed volumes in FIGS. 5-7.

The general approach to the Volume Differentiation and Removal (VDR) methodology illustrates various beneficial features of the methods and of the various arrays disclosed herein. In the following discussions, a capital letter refers to the measured voxel and a lower case letter refers to the sub-voxel (a portion of a voxel, where a compilation of all sub-voxels form a whole voxel). Numbers following the voxel or sub-voxel denote the numbered electrodes which generate/receive the signal(s) passing through the MUT (e.g., MUT 250). Referring to FIG. 5, an example four electrode linear sensor array 300 is illustrated, wherein each electrode E1, E2, E3, E4 may either be a transmitting or a receiving electrode, for transmitting or receiving a set of tomographic signals through the MUT 250 (including layers L1, L2, L3, etc. of the MUT 250). According to various embodiments, for any measurement, there is a two-electrode pairing including one transmitting and one receiving electrode (and, in this example up to three receiving electrodes). Based upon, for example, a known strength and frequency of the transmitted tomographic signal(s), a configuration of transmitting/receiving electrodes, a strength/frequency of the return tomographic signal(s), as well as a type of the MUT 250 (e.g., a general composition, known material properties, and/or a depth of penetration), various embodiments include determining characteristics (e.g., density, composition/sub-composition, etc.) of a portion (e.g., volume, sub-volume) of the MUT 250. Also illustrated are the measured volumes A12, A23, A34, B13, B24, and C14 in the MUT 250. These measured volumes are related to the three layers of interest (L1, L2, L3) in the MUT 250. The equal center-to-center spacing of communicating electrodes (e.g., E1, E2, E3, E4) is determined by the thickness or depth of the layers (L1, L2, L3) of the MUT 250 that are to be characterized. FIG. 6 illustrates several close-up views of volumes A, B13 and C14 from FIG. 5. As shown, the depth into the MUT 250 that is detectable by the electrodes is approximately equal to one-half the spacing between the centers of communicating electrodes, D. FIG. 6 also provides an illustration of the size of the measured voxels A, B, and C. FIG. 7 is a schematic depiction illustrating the relative sizes of the measured voxels (C14, B13, A12) along with the computed sub-voxels (a12, b13 and c14, respectively) from FIG. 5. The measured voxel A is the same size as the computed sub-voxel a; voxel B is twice the size of sub-voxel b; and voxel C is three times the size of sub-voxel c. FIG. 8 is a schematic depiction illustrating the arrangement of sub-voxels in a five-electrode array 500, which is used to describe more detail of the VDR approach according to various embodiments. It is understood that to characterize a greater number layers, a greater number of electrodes could be added to the array. For example in FIG. 8, a measured voxel D could be obtained by passing the signal between electrodes 1 and 5.

Figure 9:
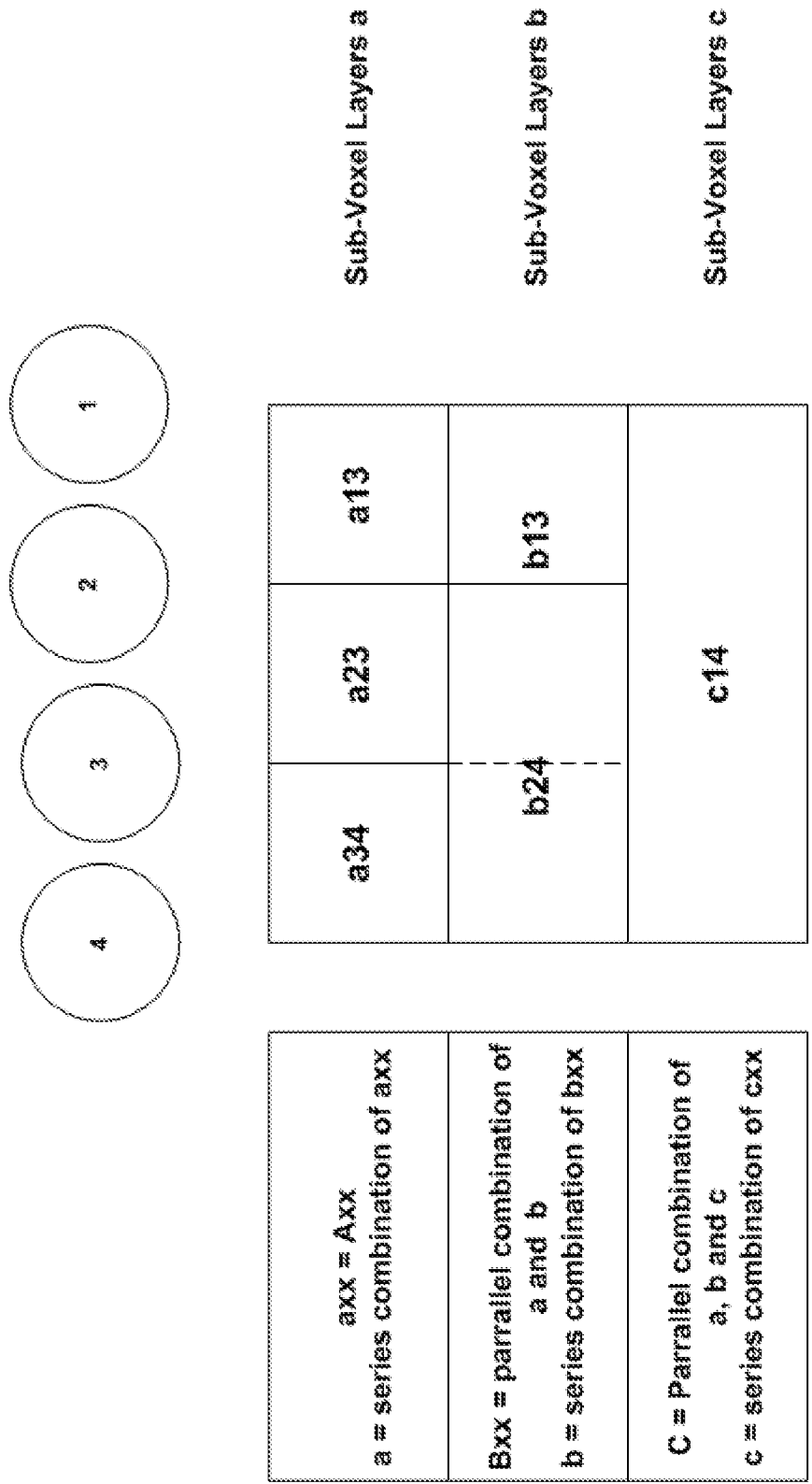
FIG. 9 is a schematic illustration of the first level of measured and computed volumes with the relevant equations, for FIGS. 5-8.
Figure 10:
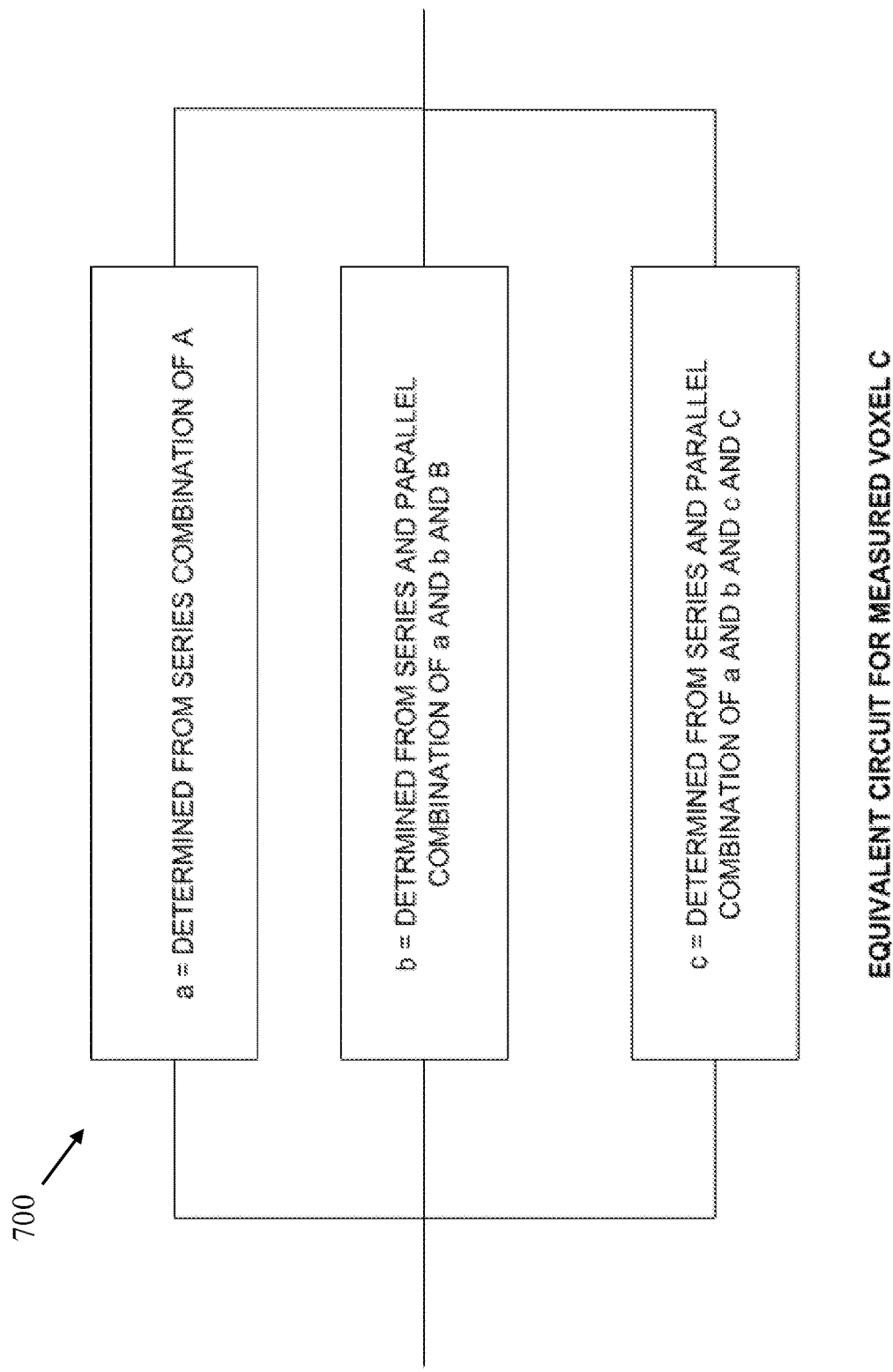
FIG. 10 is a schematic illustration of an equivalent circuit used for the measured voxel C, according to various embodiments.

One approach according to various embodiments is to collect multiple two-electrode data and to compute the values of the sub-voxels from the voxel data, and to combine the sub-voxels into voxel segments to compute other sub-voxels using the voxel segments and the voxel data. This process is illustrated in the schematic diagram in FIG. 9, which illustrates sub-voxel layers a, b, and c, corresponding to a four-electrode array (where electrodes are indicated by circular elements 1, 2, 3 and 4, respectively) such as those shown and described with reference to FIGS. 8 and 9. The impedance values of sub-voxels axx are identical to voxel Axx. Assuming volumes B13 and B24 have equivalent physical properties and, therefore, impedance characteristics, the sub-voxels b13 and b24 are computed assuming b13 and b24 are in parallel with a13 and a24. Sub-voxel a13 is the series combination of A12 and A23. Sub-voxel a24 is the series combination of A23 and A34. The sub-voxels are serially combined to form voxel segment b. Voxel segments a and b are combined in a parallel fashion with sub-voxel c14 to represent voxel C14. FIG. 10 illustrates a schematic depiction of the equivalent circuit model 700 for voxel C from FIG. 9. The equivalent circuit model 700 allows for the computation of sub-voxel c14 (FIG. 9). The mathematical process used to calculate the sub-voxel value c14 is illustrated in the equations and corresponding schematic depictions of the voxel/sub-voxel combinations shown in FIG. 11, FIG. 12, and FIG. 13.

Figure 11:
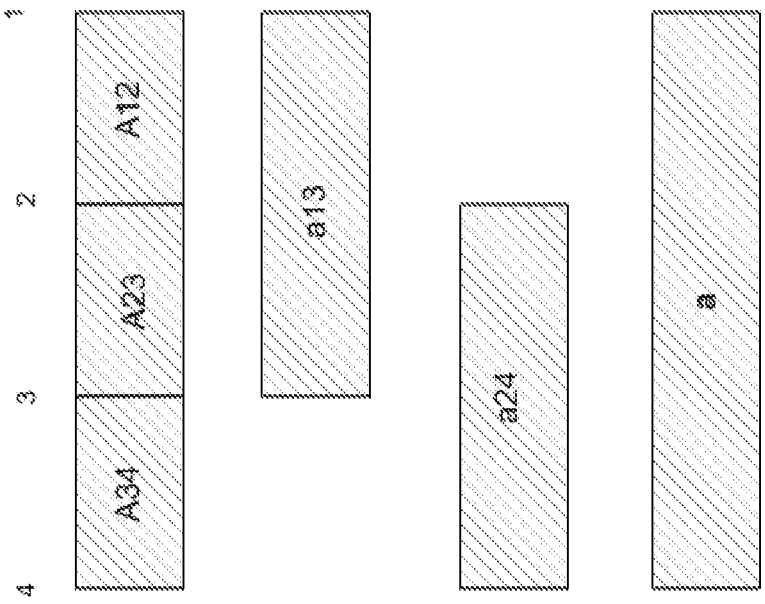
FIG. 11 is a schematic illustration of the second level of measured and computed volumes with the relevant equations for Voxel A, according to various embodiments.
Figure 12:
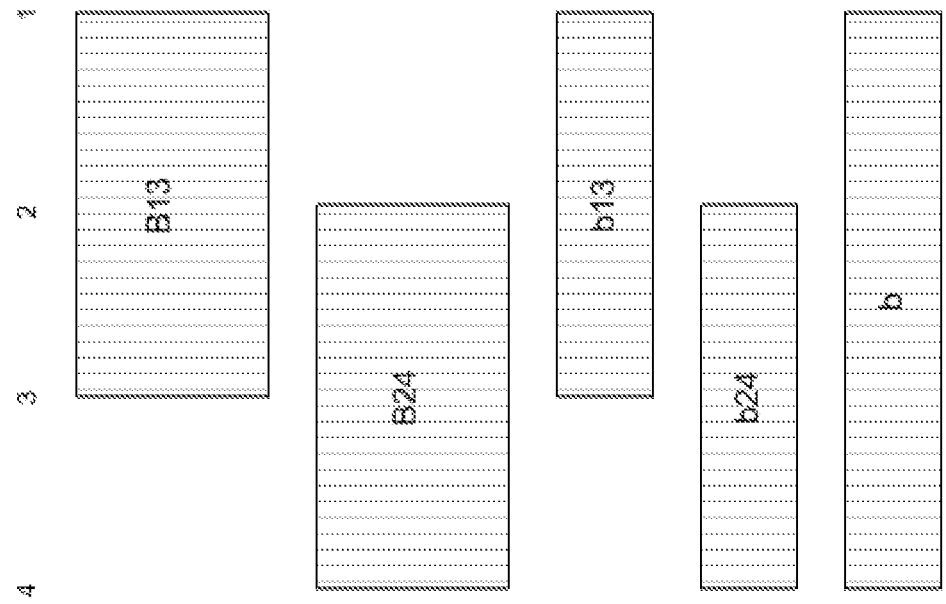
FIG. 12 is a schematic illustration of the third level of measured and computed volumes with the relevant equations for Voxel B, according to various embodiments.
Figure 13:
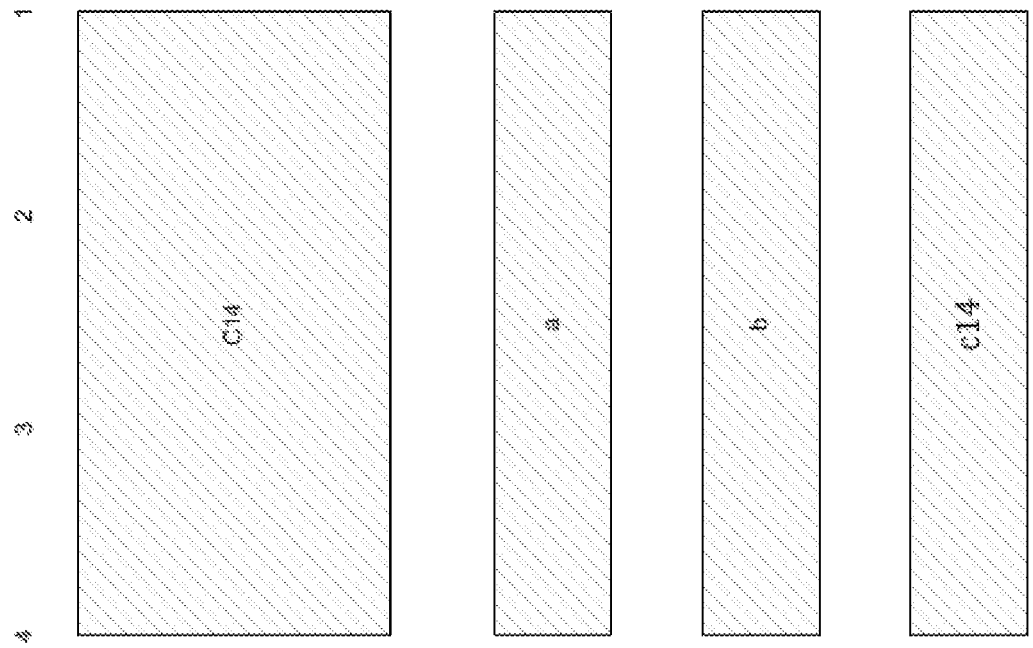
FIG. 13 is a schematic illustration of the third level of measured and computed volumes with the relevant equations for Voxel C, according to various embodiments.

The general form of the equations depicted in FIGS. 11-13 according to various embodiments is presented as follows:

$$Z_{a(n,n+1)} = Z_{A(n,n+1)}$$

$$Z_{b(n,n+2)} = \frac{(Z_{A(n,n+1)} + Z_{A(n+1,n+2)}) * Z_{B(n,n+2)}}{(Z_{A(n,n+1)} + Z_{A(n+1,n+2)}) - Z_{B(n,n+2)}}$$

$$Z_{b(n+1,n+3)} = \frac{(Z_{A(n+1,n+2)} + Z_{A(n+2,n+3)}) * Z_{B(n+1,n+3)}}{(Z_{A(n+1,n+2)} + Z_{A(n+2,n+3)}) - Z_{B(n+1,n+3)}}$$

$$Z_{a(n,n+3)} = Z_{A(n,n+1)} + Z_{A(n+1,n+2)} + Z_{A(n+2,n+3)}$$

$$Z_{b(n,n+3)} = \alpha Z_{b(n,n+2)} + (1-\alpha) * Z_{b(n+1,n+3)}$$

$$Z_{c(n,n+3)} = \frac{Z_{a(n,n+3)} * Z_{b(n,n+3)} * Z_C(n, n+3)}{(Z_{a(n,n+3)} * Z_{b(n,n+3)}) - (Z_{a(n,n+3)} + Z_{b(n,n+3)}) * Z_{C(n,n+3)}}$$

According to various embodiments, the above equations may be modified based upon the geometry of the electrode arrangement to account for the differences between the measured volume of the MUT (e.g., MUT 250) and the assumed shape of the voxels and sub-voxels in that volume. To account for relative changes in the geometry of electrode arrangements, a geometry factor may be determined and applied to the measured impedance of the voxels as follows:

$$Z_{A(n,n+1)}$$

$$Z_{b(n,n+2)} = \frac{(\gamma_A Z_{A(n,n+1)} + \gamma_A Z_{A(n+1,n+2)}) * \gamma_B Z_{B(n,n+2)}}{(\gamma_A Z_{A(n,n+1)} + \gamma_A Z_{A(n+1,n+2)}) - \gamma_B Z_{B(n,n+2)}}$$

$$Z_{b(n+1,n+3)} = \frac{(\gamma_A Z_{A(n+1,n+2)} + \gamma_A Z_{A(n+2,n+3)}) * \gamma_B Z_{B(n+1,n+3)}}{(\gamma_A Z_{A(n+1,n+2)} + \gamma_A Z_{A(n+2,n+3)}) - \gamma_B Z_{B(n+1,n+3)}}$$

$$Z_{a(n,n+3)} = \gamma_A Z_{A(n,n+1)} + \gamma_A Z_{A(n+1,n+2)} + \gamma_A Z_{A(n+2,n+3)}$$

$$Z_{b(n,n+3)} = \alpha Z_{b(n,n+2)} + (1-\alpha) * Z_{b(n+1,n+3)}$$

$$Z_{c(n,n+3)} = \frac{Z_{a(n,n+3)} * Z_{b(n,n+3)} * \gamma_C Z_C(n, n+3)}{(Z_{a(n,n+3)} * Z_{b(n,n+3)}) - (Z_{a(n,n+3)} + Z_{b(n,n+3)}) * \gamma_C Z_{C(n,n+3)}}$$

where: A, B, and C are the measured voxel volumes;
a, b, and c are the computed sub-voxel properties;
n is the electrode array number;
α is the relative contribution of Zb(n+1, n+3) relative to Zb(n+1, n+3); and
$\gamma_x$ is a geometry factor for the xth voxel. The geometry factor is a correction applied to the planar electrodes to correlate the values read with a parallel plate electrode ε. The parallel plate equation is:

$$C = \frac{A}{d}\varepsilon;$$

where:
C is the capacitance;
ε is the dielectric; and
A/d is equivalent to a geometry factor.

The ability to secure the impedance measurements used to apply the above disclosed VDR methodology as explained above can depend upon the corresponding design and operation of the sensor array. Some array designs have been previously disclosed in the above-referenced issued patents and patent applications. In the following paragraphs, five linear and planar electrode array configurations are presented which provide various improvements over those referenced conventional approaches. As indicated above, the VDR is applied to compute the impedance for each sub-voxel at each frequency in the range of applied frequencies to secure the impedance characteristics of each sub-voxel at each frequency. These data may then be applied using various spectrographic methods to characterize the desired property or properties of the MUT.

Figure 14:
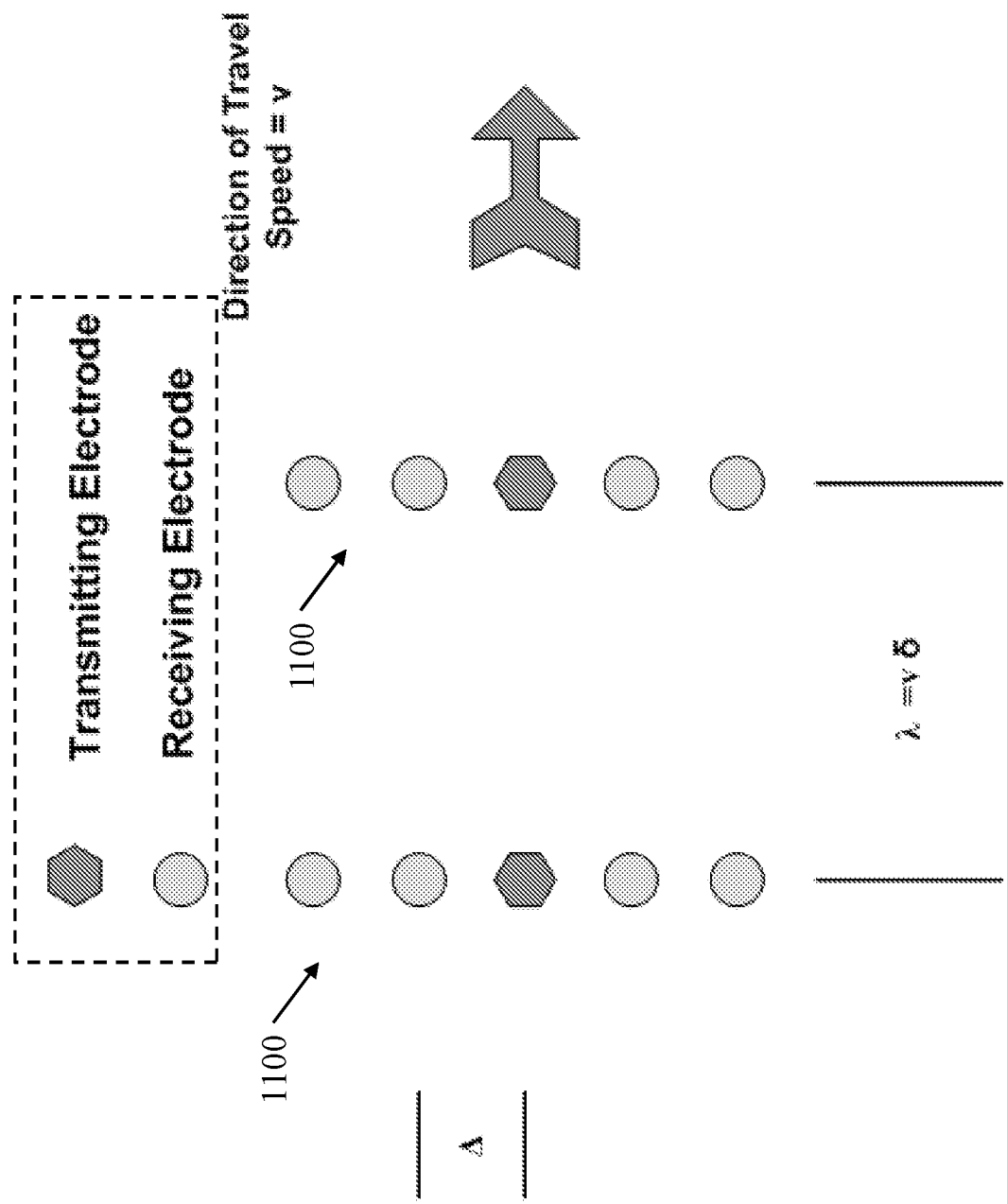
FIG. 14 is a schematic illustration of a moving linear array according to various embodiments.
Figure 15:
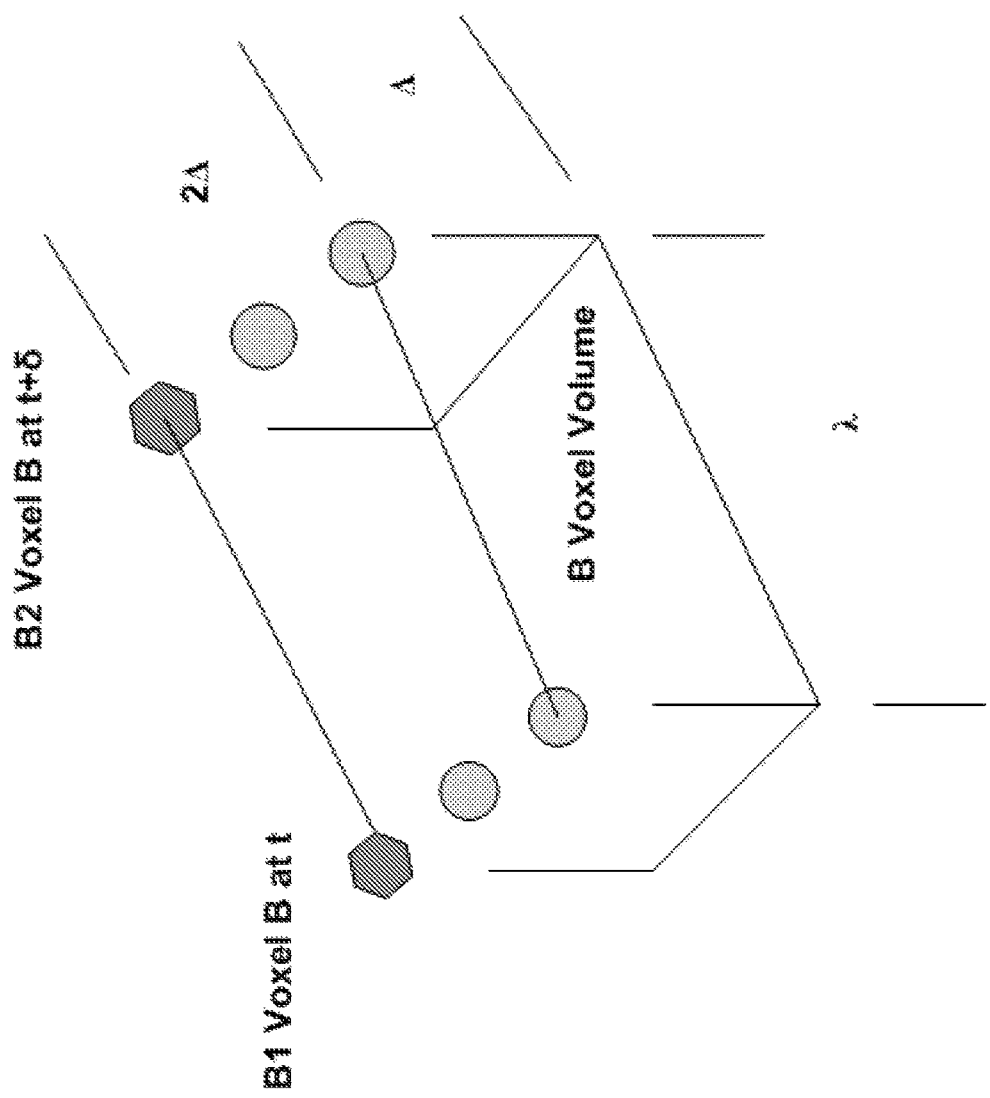
FIG. 15 is a schematic illustration of a three dimensional voxel derived from the movement of a linear array, according to various embodiments.

In U.S. provisional patent application No. 61/703,488, the movement of a sensor array is discussed as a method to detect features in an MUT. FIG. 14 illustrates the movement of a five electrode array 1100 with a fixed arrangement of transmitting and receiving electrodes. The array 1100 has an electrode center-to-center spacing of Δ, and is traveling at a speed of v. Data is secured in time intervals of δ. Over the time interval, the array moves a distance of λ=vδ. For a B voxel, two measurements at time t and t+δ yield a three-dimensional voxel as shown in the schematic depiction of voxel B in FIG. 15. As illustrated in FIG. 15, voxel B is 2Δ wide, Δ deep and λ long. In this embodiment, the impedance characteristics of this three dimensional voxel, $\overline{B}$, is given by a series combination of the $B_t$ and the $B_{t+\delta}$ voxels, with a geometric correction factor which will vary with the size of the electrodes and the size of λ. This geometric scaling may be experimentally determined, and represented as:

$$\overline{B} = B_t + B_{t+\delta};$$

Once the impedance characteristic of the three dimensional voxels are determined, the sub-voxel information may be determined in the same manner as described above.

Figure 16:
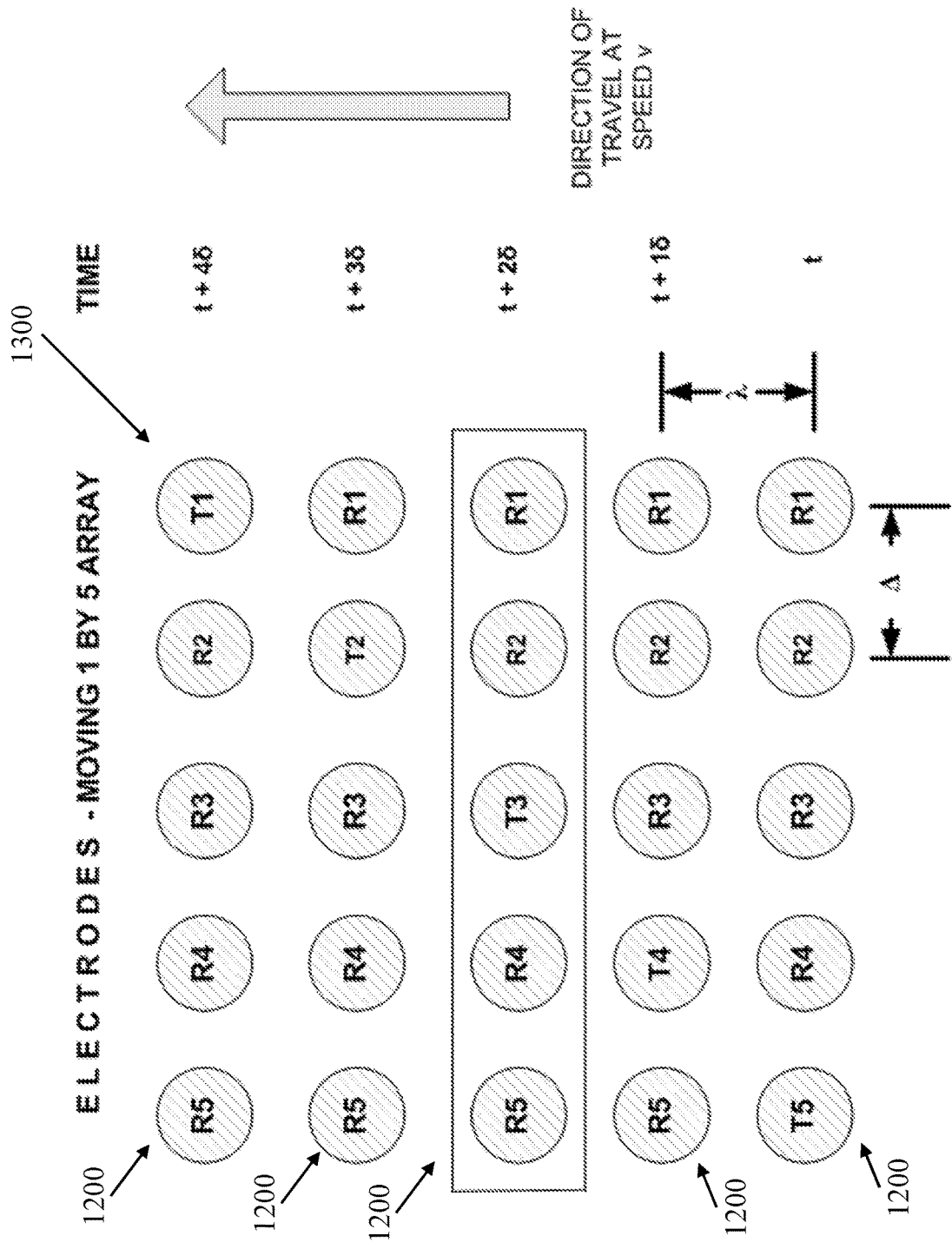
FIG. 16 is a schematic illustration of a moving linear array with the transmitting electrode change every time period 6, according to various embodiments.
Figure 17:
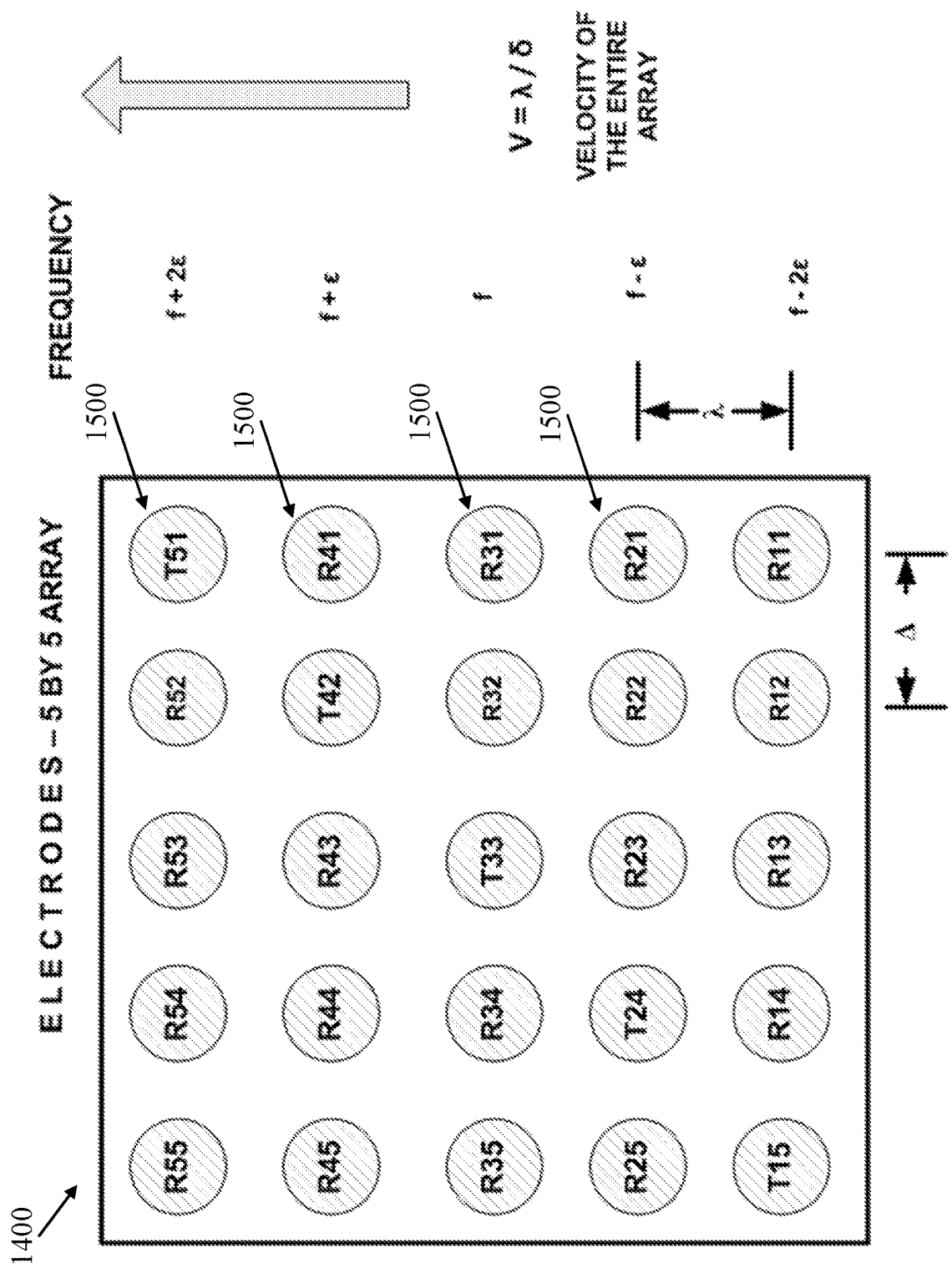
FIG. 17 is a schematic illustration of a square planar electrode array where each linear electrode array is operating at a different frequency, according to various embodiments.

The approach described with reference to FIGS. 14-15 may fail if the transmitting and receiving electrode spacing are varied (not constant). As previously discussed in conjunction with FIG. 8, according to various embodiments, each electrode in an array may either transmit or receive. This bi-modal concept is illustrated in the schematic depiction of several five-by-one linear arrays 1200 in a larger planar array 1300 (including each of the five-by-one arrays 1200) in FIG. 16. As shown, a five-electrode linear arrays 1200 scan through the five options for the transmitting electrode (T1, T2, T3, T4, T5) while the planar array 1300 is moving at a velocity of v. According to various embodiments, the transmitting electrode (TX) is switched every δ second, such that each of the five electrodes in each linear array 1200 is transmitting over the five time intervals of measurement. In this example, according to various embodiments, the distance traveled during the transmitting electrode switching process is λ=5vδ. Applicants have discovered that the size of λ may affect the ability to apply the method described above to accurately characterize the MUT (e.g., MUT 250) if changes in physical properties (e.g., density, composition, viscosity, etc.) occur in the MUT at the same scale or smaller than 2. This change in the MUT, according to various embodiments, can be used to determine the characteristic(s) of the MUT, and the detail at which the MUT may be examined. The time duration δ is dependent on the speed at which the planar array 1300 (including linear arrays 1200) is moving, the speed at which the array electronics can switch between transmitting electrodes, and the time required to process the measurement data to characterize the MUT (e.g., where processing is performed using at least one computing device, as described herein with reference to FIG. 22). The number of electrodes in the array can also affect the determination of λ. An alternate embodiment of an array 1400 is schematically depicted in FIG. 17. In this embodiment, the array 1400 includes a planar array composed of five rows of linear five-electrode arrays 1500, depicted as moving at a velocity, v. The transmitting electrode (TXX) in each linear array 1500 is fixed, while each transmitting linear array 1500 is operated at a different frequency with a separation of Hz. This frequency separation is sized such that the signals from distinct linear arrays 1500 may be isolated electronically, and such that the total change in frequency does not result in a change in the interpretation of the physical parameters of the MUT that are of interest. In various embodiments, the number of rows of linear arrays 1500 in the planar array 1400 is equal to the number of electrodes in each of the linear arrays 1500 (e.g., 5 rows of linear arrays 1500 with 5 electrodes each).

Figure 18:
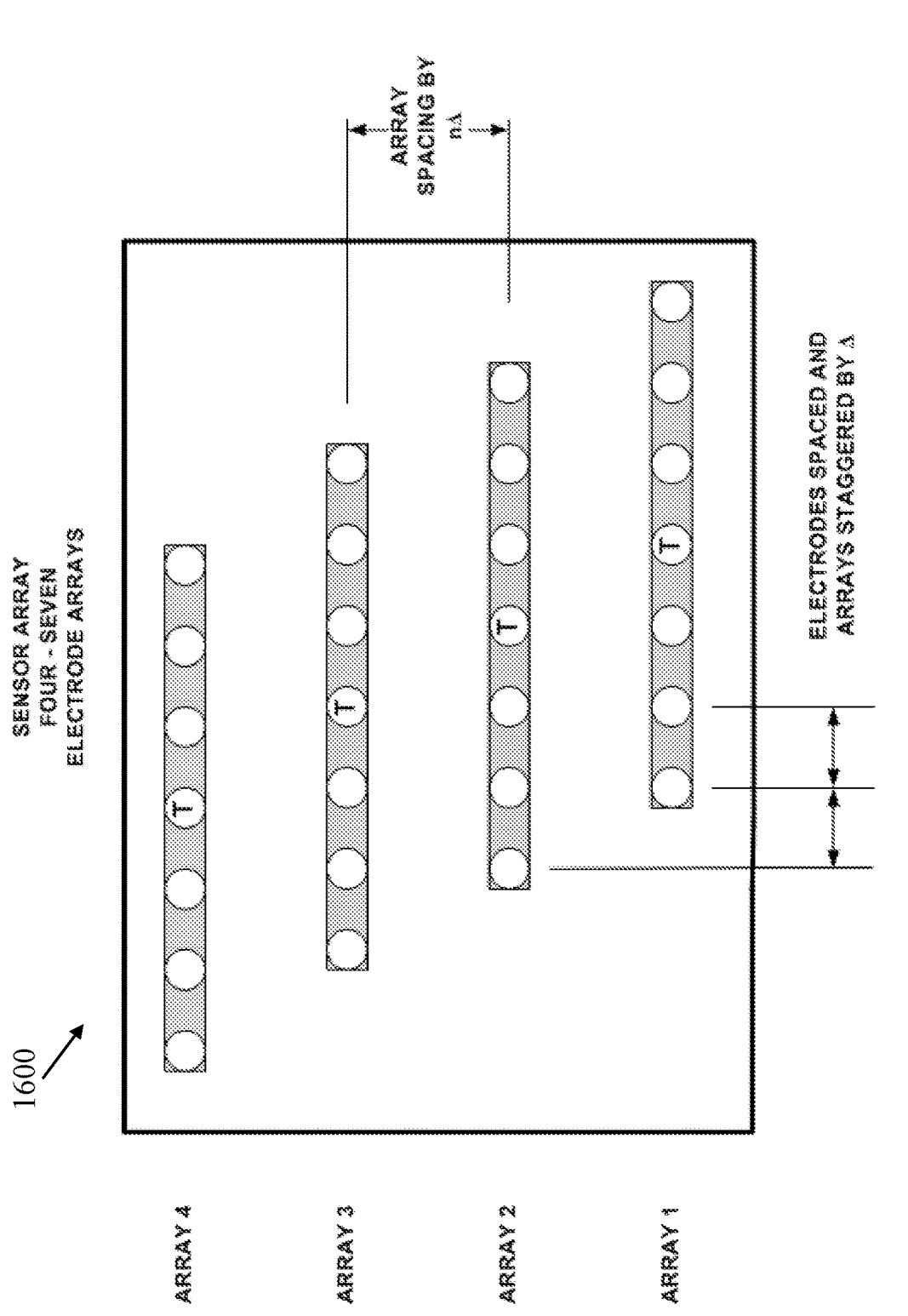
FIG. 18 is a schematic illustration of a planar array consisting of staggered linear electrodes, according to various embodiments.
Figure 19:
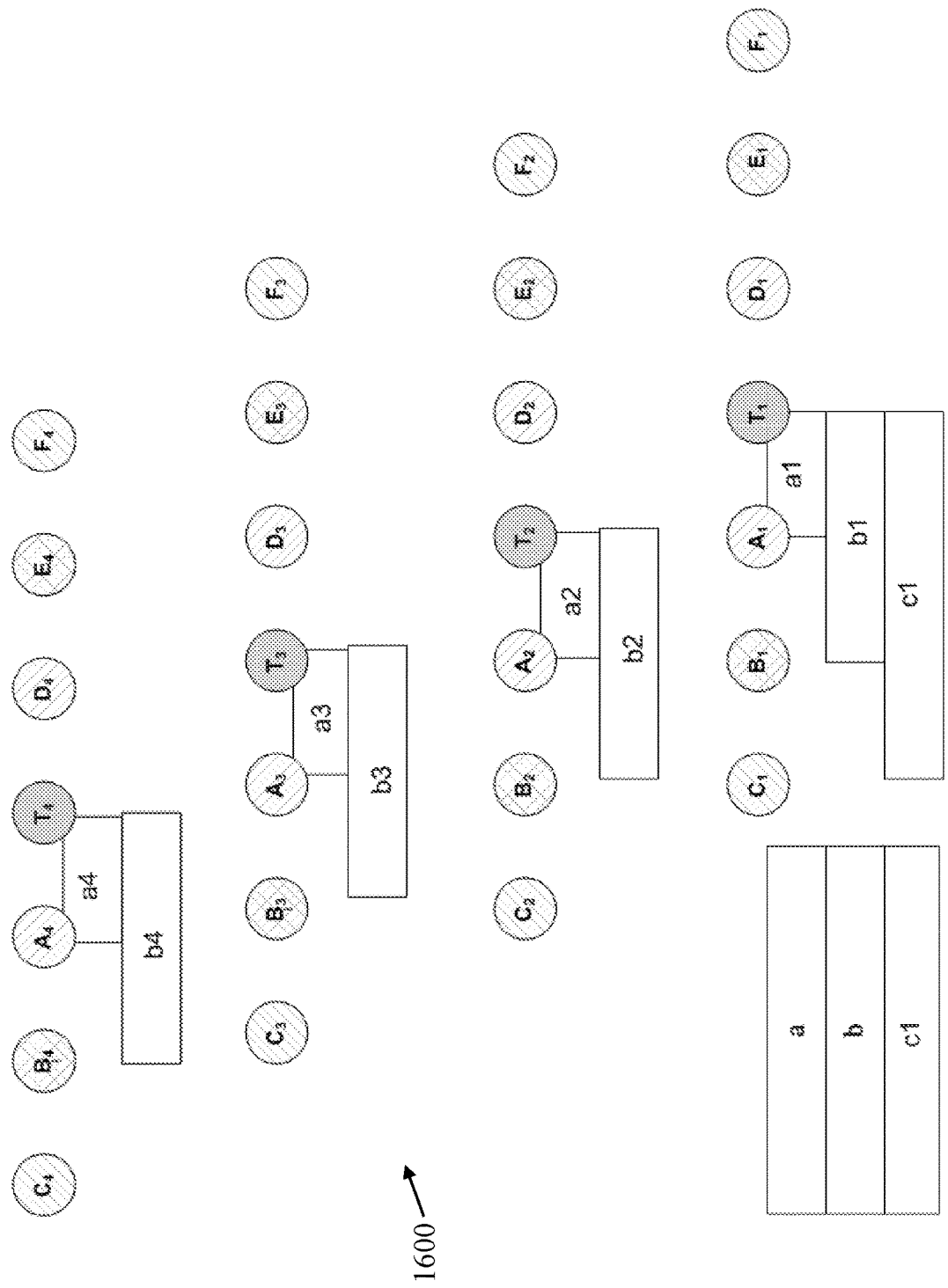
FIG. 19 is a schematic depiction of the planar array of FIG. 18, further illustrating how characteristics of the subvoxels can be determined using the array according to various embodiments.

An alternative embodiment of a planar array 1600 is shown in FIG. 18, which uses four linear arrays (Array 1, Array 2, Array 3, Array 4) orientated with each array (1, 2, 3, 4) being offset from its adjacent array (1, 2, 3, 4) by the center-to-center spacing between adjacent electrodes in each of Array 1, Array 2, Array 3 and Array 4. If variations in the properties of the MUT are small in the horizontal plane relative to the size of the planar array 1600, this alternative embodiment may be beneficial in determining characteristics of the MUT. Further, if the thickness of the MUT (e.g., thickness of particular layers or overall thickness) is small, this embodiment can enable accurate measurement of the MUT. For example, some coatings are placed on critical parts in machinery, with each coating thickness on the order of 50 microns. In this example, the electrode spacing (in each Array) can be on the order of approximately 50 microns in order to see at least two layers of the coating. The total size of the planar sensor array 1600 with four seven-electrode linear arrays (Array 1, Array 2, Array 3, Array 4) can be on the order of approximately 500 microns (0.02 inches) squared. In this type of planar array 1600, the number of electrodes in each array (Array 1, Array 2, etc.) is an odd number, and the transmitting electrode (T) is fixed as the middle electrode in each array (Array 3, Array 4, etc.). FIG. 19 is a schematic depiction of the planar array 1600 of FIG. 18, further illustrating how characteristics of the sub-voxels (e.g., b4, b3, b2, etc.) can be determined from this type of array 1600 according to various embodiments described herein. In this type of array 1600, according to some embodiments, each of the seven-electrode linear arrays (Array 1, Array 2, etc.) may be operated at different times, with the same frequency. In some embodiments, the seven-electrode linear arrays (Array 1, Array 2, etc.) may be operated simultaneously at slightly different frequencies, as described with reference to various embodiments described herein.

Figure 20:
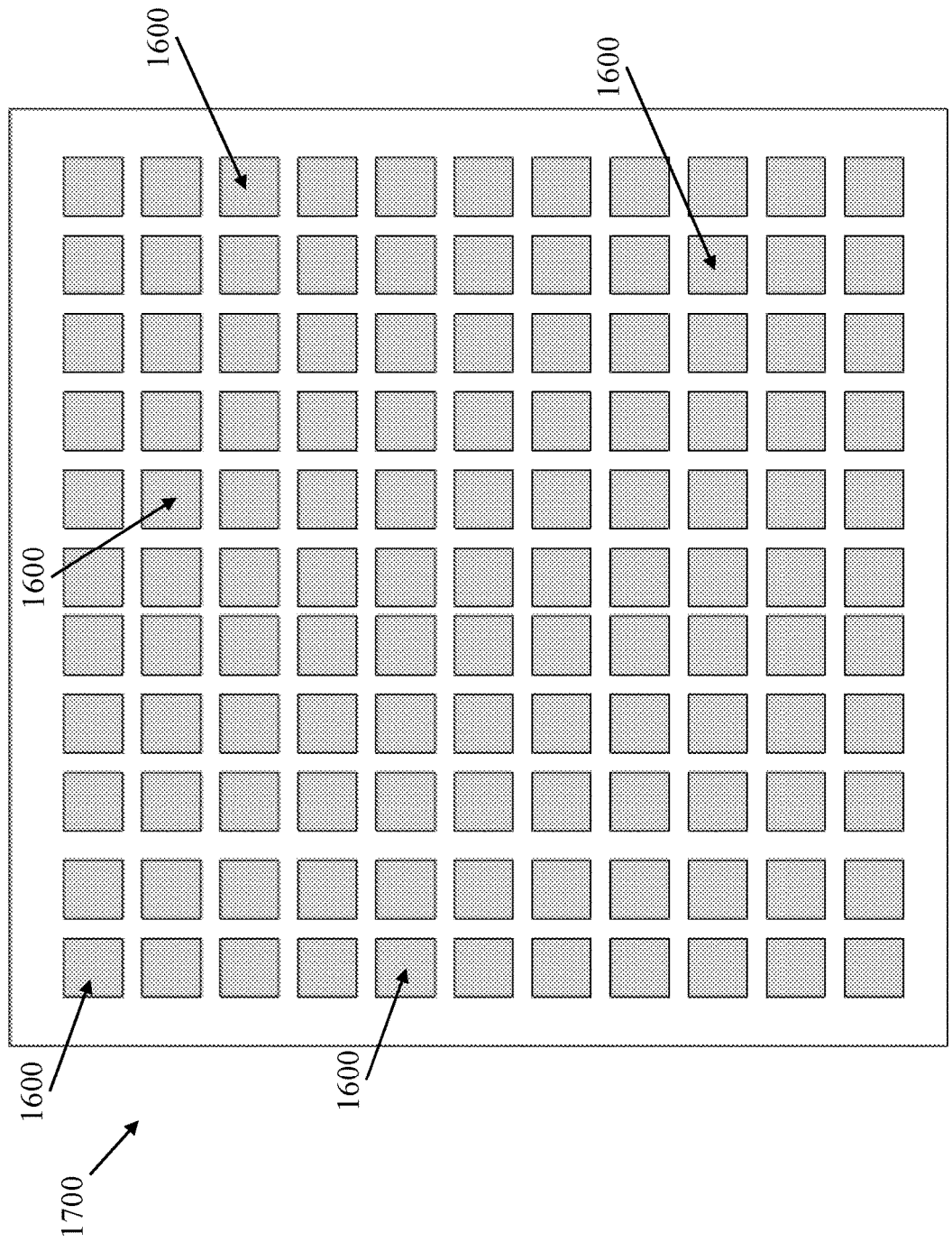
FIG. 20 is a schematic illustration of the placement of individual planar sensor arrays onto a large inspection matrix, according to various embodiments.

Given the potentially very small size of the planar array 1600 in order to detect relatively thin regions of an MUT, a method to cover larger areas of the MUT can include combining a number of the relatively smaller planar arrays 1600 located on a lager inspection fixture 1700, depicted schematically in FIG. 20. In this example illustration, the inspection fixture 1700 includes 121 of the planar arrays 1600 of FIGS. 18-19, located on a one-inch grid. According to various embodiments, many methods are available to scan through the planar arrays 1600 to determine characteristics of the MUT. For example, each planar array 1600 may be treated as a pixel, and can be scanned by any of the various available electronic scanning methods known in the art.

Figure 21:
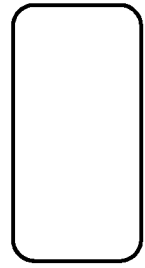
FIG. 21 shows schematic depictions of example electrode shapes according to various embodiments.
Figure 21:
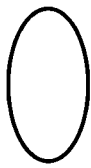
Figure 21:
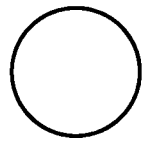

The design of the individual electrodes in the various arrays discussed with reference to FIGS. 4-20 may be circular in shape. However, in some embodiments, a circular-shaped electrode may limit the potential of field concentration available if the desired area of detection in the MUT includes a corner or a point. In various embodiments, at least one of the electrodes has an ellipsoid shape. In various other embodiments, at least one of the electrodes has a rectangular shape with rounded corners. FIG. 21 shows schematic depictions of example electrode shapes, which can be used in any of the electrode arrays shown and described herein according to various embodiments. The Applicants have also found that field concentrations may distort the electromagnetic field and affect the raw data obtained from the MUT. Accordingly, in various embodiments, the electrodes may have a uniform area to match their signal generation capacity with corresponding receiving capacity. In some cases, the diameter of the electrodes relative to the distance between the centers of the electrodes, A, may vary. The Applicants have further discovered that there may be a tradeoff between the electromagnetic field strength of the array, the geometry factor of the array, and the signal-to-noise ratio of the measurement obtained by the array. Applicants have further discovered that these factors are not determinant a priori to establish the optimum area of the electrode.

Various approaches described allow for determining a physical property of a sub-voxel or a number of sub-voxels of the MUT. In various embodiments, a number of measurements of the physical property(ies) of interest are measured by conventional means and correlated with the measured variations of the measured (and computed) complex impedance (of the voxels and sub-voxels) using the arrays/ systems/approaches described herein. In various embodiments, the number of measurements can be sufficiently large such that the resulting correlation is statistically significant. The impedance measurements can be made with the same type of array that will be used to inspect unknown MUTs, or in other embodiments, a parallel plate electrode arrangement may be used. Regardless of the array geometry, the measurements may also be made over a range of frequencies. Further embodiments include a method of developing an algorithm to correlate the physical property to the measured impedance (of the voxel or sub-voxel over the selected range of frequencies), which may use any number of well known correlation methods such as analysis of variations (ANOVA), neural networks, and multiple regressions. A determination as to which process, impedance characteristic(s) and frequency range may ensure that the best fit may be made by selection of the one that provides the most statistically significant results.

Figure 22:
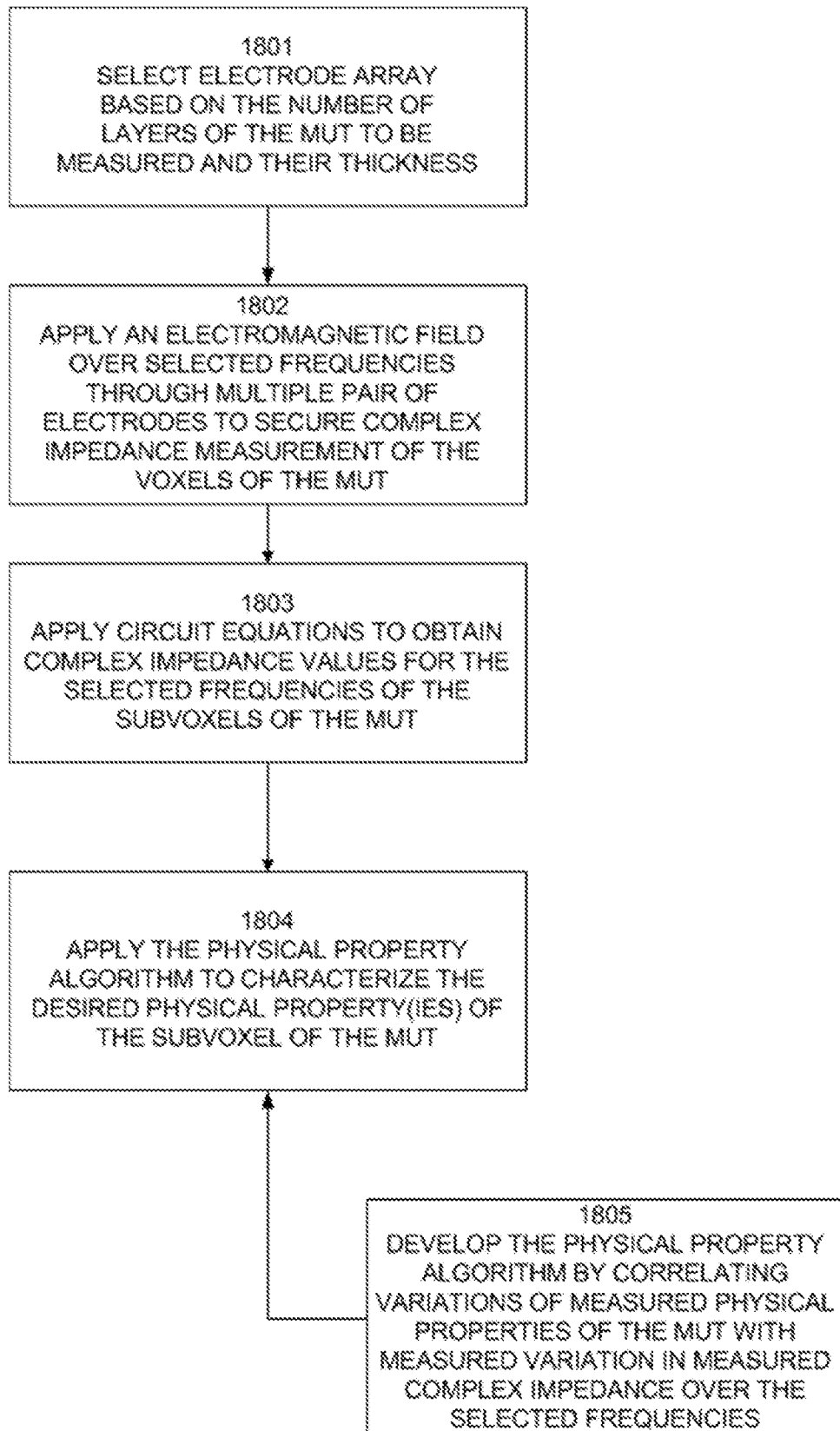
FIG. 22 is a flow chart illustrating a process according to various embodiments.

FIG. 22 presents a flow diagram illustrating processes to determine at least one characteristic (e.g., physical property) of a sub-voxel of a MUT (e.g., MUT 250, FIG. 4). The first process (1801) can include selecting the appropriate type of array for use with the MUT, and selecting the number and thickness of each layer that is to be measured, along with an overall thickness of the layers to be measured. The number and thickness of individual layers, as well as overall thickness, can determine the number of electrodes in the array, and the corresponding center-to-center spacing of adjacent electrodes useful to detect characteristics of the MUT. The next process (1802) can include coupling the sensor array to an impedance measuring system (e.g., at least one computing device) to obtain the complex impedance values for the voxels of interest in the MUT. The measurements can be made over the frequency range that corresponds with the required inputs to the physical property algorithm. The next process (1803) includes utilizing the circuit equations described according to various embodiments herein to compute the desired impedance characteristic of the sub-voxels, over the frequency range that corresponds with the required inputs to the physical property algorithm. The final process in this method (1804) can include using the sub-voxel impedance values (along with the physical property algorithm described according to various embodiments) to determine the corresponding characteristic (e.g., physical property) of that sub-voxel of the MUT. An optional additional process (1805) can include developing the physical property algorithm which is applied in step 1804, prior to applying that algorithm.

Figure 23:
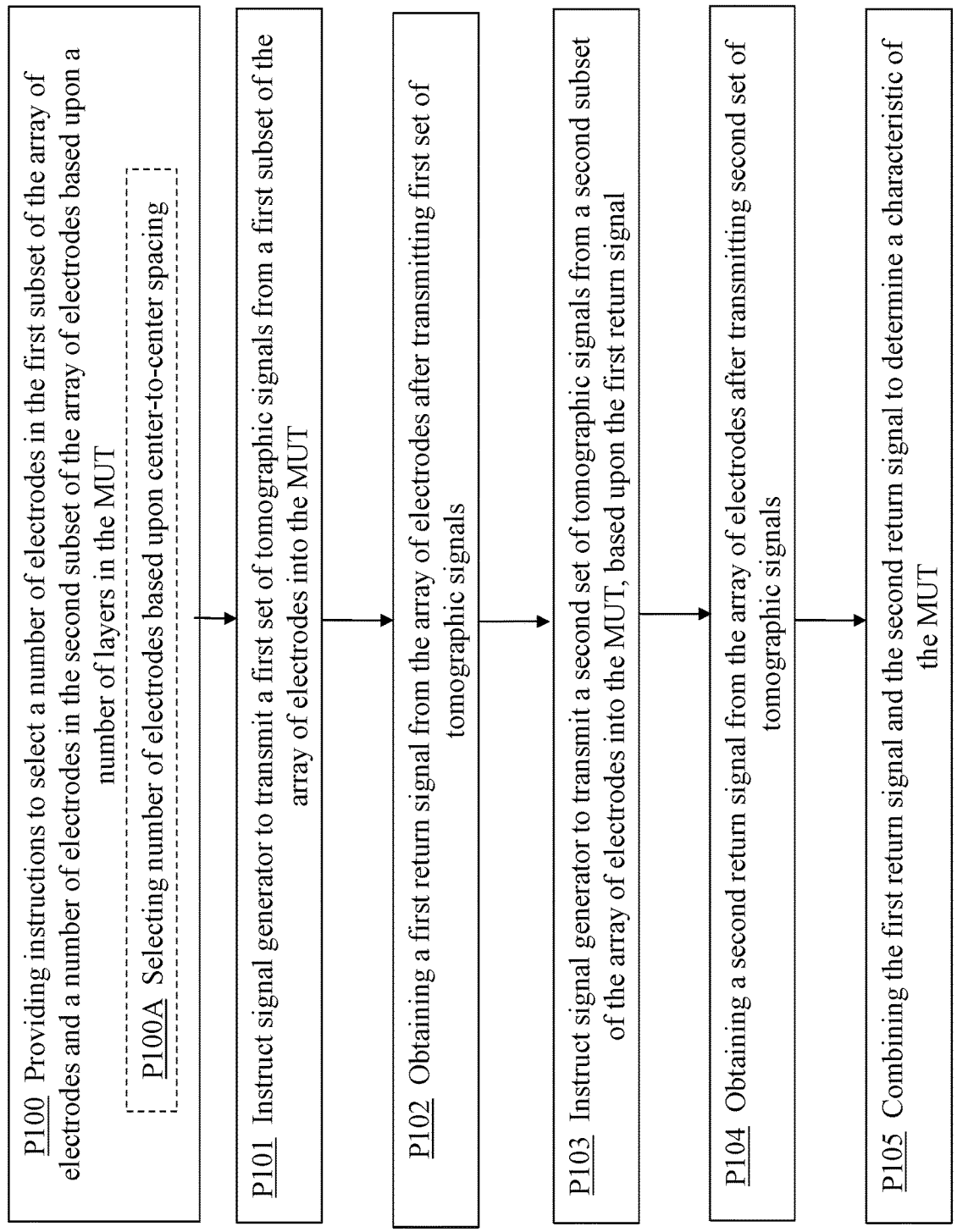
FIG. 23 is a flow chart illustrating a process according to various embodiments.

As described herein, various aspects of the invention can include computer implemented methods, systems and computer program products for performing a series of functions. FIG. 23 shows a flow diagram depicting a method according to various embodiments of the disclosure applying tomography. The method can be used to characterize select volumes of an MUT using an array of electrodes. As shown, the flow diagram can include processes including:

Process P101: instructing a signal generator (within sensor array 2120, FIG. 25) to transmit a first set of tomographic signals from a subset of the array of electrodes into the MUT 250 and obtain the return signal at that frequency for that subset of the array of electrodes;

Process P102: obtaining a first return signal from the array of electrodes after the transmitting of the first set of tomographic signals;

Process P103: instructing the signal generator (within sensor array 2120, FIG. 25) to transmit a second set of tomographic signals from a second subset of the array of electrodes into the MUT 250 based upon the first return signal, the second subset of the array of electrodes including at least one electrode not included in the first subset of the array of electrodes. Referring to FIGS. 18-19, an example scenario illustrating distinct subsets in the array of electrodes can include a first subset of electrodes, e.g., array 4, and a second subset of electrodes, e.g., array 2, array 3 or array 1. In some cases, these individual arrays (array 1, array 2, etc.) are deemed "sub-arrays" in an overall planar array (as shown in FIG. 18). According to some embodiments, sub-arrays can include overlapping electrodes, with at least one electrode present in a first sub-array that is not present in a second sub-array;

Process P104: obtaining a second return signal at the array of electrodes after the transmitting of the second set of tomographic signals; and Process P105: combining the first return signal and the second return signal to determine a characteristic of the MUT 250. According to various embodiments, the first return signal and the second return signal each include complex impedance data about at least one of a volume or a voxel of the MUT 250. In some embodiments, the combining of the first return signal and the second return signal to determine a characteristic of the MUT 250 includes applying at least one of series or parallel circuit theory to the complex impedance data based upon a location of the first subset of the array of electrodes and the second subset of the array of electrodes in the electrode array. The series and parallel circuit approach is described with respect to various embodiments herein. According to various embodiments, the complex impedance data about the at least one of the volume or the voxel is correlated with physical properties of the MUT 250.

In various embodiments, prior to process P101, preliminary process P100 can include providing instructions to select a number of electrodes in the first subset of the array of electrodes and a number of electrodes in the second subset of the array of electrodes based upon a number of layers in the MUT 250. In various embodiments, this preliminary process P100 can include Process P100A: selecting the number of electrodes in the first subset and the number of electrodes in the second subset based upon a center-to-center spacing between adjacent electrodes in the array of electrodes.

As noted herein, according to various embodiments the array of electrodes (electrode array) includes a linear array of equally spaced electrodes configured to operate at a single frequency. Further, in some embodiments, the instructing of the signal generator (within sensor array 2120, FIG. 25) to transmit the first set of tomographic signals, the obtaining of the first return signal, the instruction of the signal generator (within sensor array 2120, FIG. 25) to transmit the second set of tomographic signals, and the obtaining of the second return signal are performed while the electrode array is in motion parallel to a plane co-planar with the array of electrodes, and wherein the first return signal and the second return signal are separated at a time interval, $\delta$.

Figure 24:
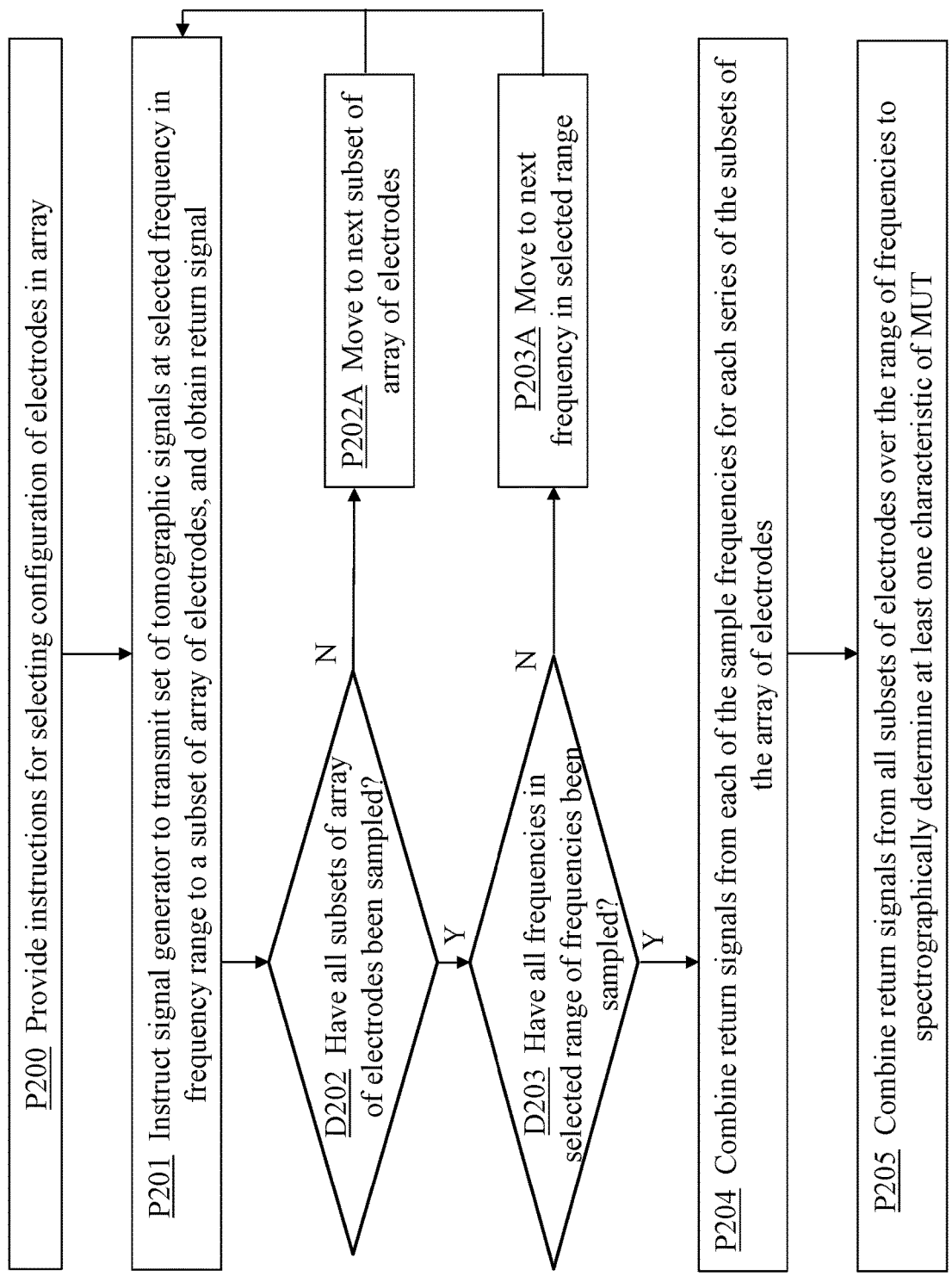
FIG. 24 is a flow chart illustrating a process according to various embodiments.

FIG. 24 shows an illustrative flow diagram depicting a method according to various embodiments applying both tomography and spectroscopy. The method can include:

Process P200: Providing instructions for selecting a configuration of electrodes in the array of electrodes, including electrode subsets, based upon at least one of: A) Number of layers in the MUT 250; B) Center-to-center spacing between electrodes based upon the thickness of the MUT 250; C) Frequency range of data collection based upon the spectrographic impedance characteristics of desired MUT 250 property/properties; and/or D) Subset arrangements of the array of electrodes, based upon requirements of the application of the series and/or parallel circuit approach to compute the complex impedance for each voxel and/or subvoxel of the MUT 250;

P201: Instructing signal generator (within sensor array 2120, FIG. 25) to transmit set of tomographic signals at selected frequency in frequency range to a subset of the array of electrodes, obtain return signal;

D202: Have all subsets of array of electrodes 200 sampled?;

P202A: No to D201A, move to next subset of array of electrodes; loop back to P201;

D203: Yes to D201A, have all frequencies in the selected range of frequencies been sampled?;

P203A: No to D203, move to the next frequency in the selected range of frequencies, loop back to P201;

P204: Combine return signals from each of the sample frequencies for each series of the subsets of the array of electrodes, using series and/or parallel equivalent circuit approach described herein to compute complex impedance for each voxel and/or sub-voxel of MUT 250; and P205: Combine return signals from all subsets of electrodes over the range of frequencies to spectrographically determine at least one physical characteristic of the MUT 250.

Figure 25:
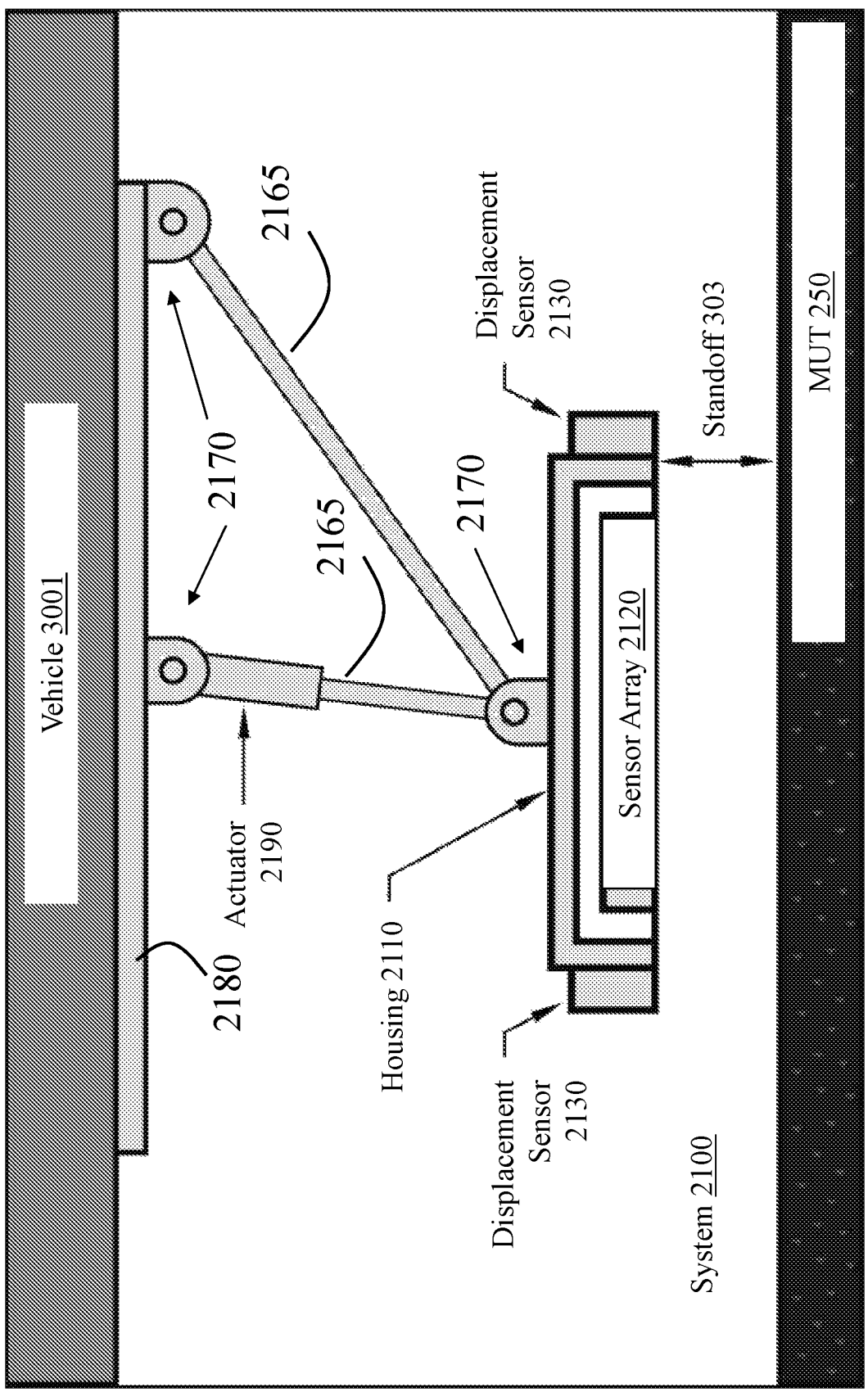
FIG. 25 is a schematic two-dimensional illustration of a system according to various embodiments of the disclosure.
Figure 26:
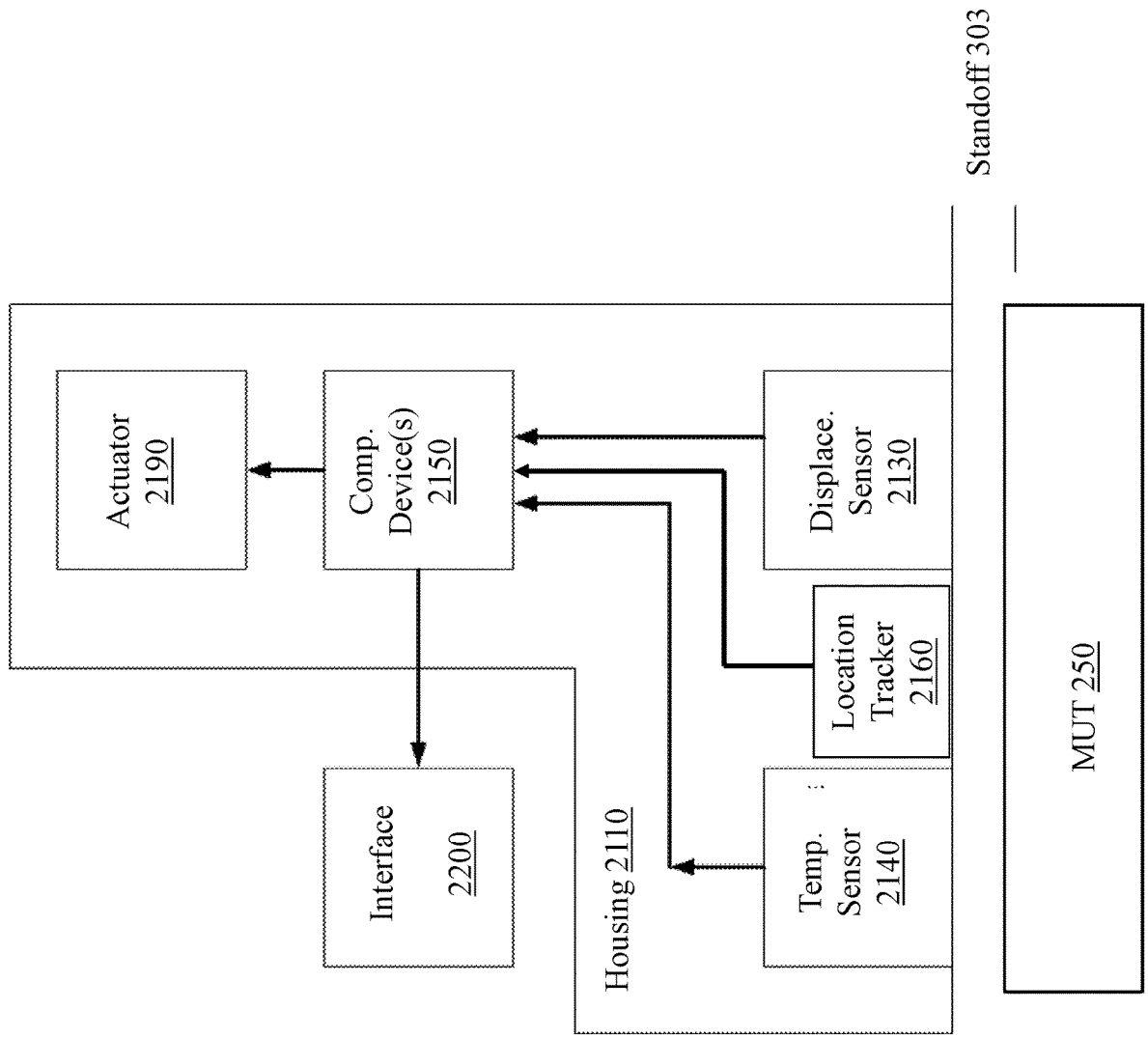
FIG. 26 is a schematic illustration of a sample sensor system according to various embodiments of the disclosure.

FIG. 25 shows a schematic side view of an embodiment of a physical system 2100, according to various embodiments of the disclosure. FIG. 26 shows a schematic data-flow diagram depicting data-flow within system 2100 (FIG. 25) according to various embodiments of the disclosure. As shown, with reference to FIG. 25 and FIG. 26, system 2100 can include a housing 2110, which includes a sensor array 2120 (e.g., including any sensor array configuration described herein, such as a two-electrode sensor array) and a displacement sensor 2130 (e.g., including any conventional optical, thermal, or other sensors known in the art). The housing 2110 can further house at least one temperature sensor 2140 (e.g., a conventional temperature sensor), a location tracker 2160 (such as a GPS and/or GIS device which obtains locational information), and at least one computing device 2150 (e.g., including a conventional processor, memory, input/output interface, data store, etc.), each of which are coupled with the displacement sensor 2130 and the sensor array 2120 via conventional hard-wired and/or wireless communication. The location tracker 2160 can include a conventional location tracking device, e.g., a GPS and/or GIS device, and computing device 2150 can be configured to detect a rate of travel (speed) of the housing 2110 using geographic data from the location tracker 2160 correlated with time, as is known in the art. The housing 2110 can be coupled with at least one support arm 2165, e.g., via a hinge mechanism 2170. The at least one support arm 2165 may be coupled to a mount 2180, e.g., via additional hinge mechanisms 2170. The mount 2180 can be configured to connect with a vehicle 3001, e.g., via bolt(s), screw(s), clamp(s), etc. The system 2100 can further include an actuator 2190, e.g., a hydraulic or piezoelectric actuator, coupled with at least one of the support arm(s) 2165 to modify a position of the housing 2110 (and consequently, the sensor array 2120) relative to the MUT 250 based upon a displacement measurement from displacement sensor 2130. The actuator 2190 can communicate (e.g., via hard-wired means via support arm 2160, or via wireless means) with the at least one computing device 2150, and may receive instructions from the computing device(s) 2150 to modify a position of the housing 2110. The computing device(s) 2150 may gather data from displacement sensor(s) 2130 about a distance (e.g., standoff 303) between the sensor array 2120 and the MUT 250 (e.g., asphalt), and use that information about the distance 303 as an input to calculate at least one physical property of the MUT 250. Additionally, in various embodiments, the at least one computing device 2150 can continuously obtain data about the distance 303 between the sensor array 2120 and the MUT 250, and verify that calculations about the physical property of the MUT 250 are accurately accounting for the distance 303. In various embodiments, the topography of the MUT 250, movement of the vehicle 3001, unintentional movement of one or more of the support arms 2165, etc., may cause the sensor array 2120 to shift to a different distance from the MUT 250, which may affect the calculations regarding physical characteristics of the MUT 250. In various embodiments, a desired distance (offset) 303 is known, and is used as a basis to calculate physical characteristics (e.g., density) of the MUT 250. When the displacement sensor(s) 2130 provide data (to computing device 2150) indicating that the housing 2110 (and consequently, the sensor array 2120) has moved relative to the MUT 250 such that the desired offset 303 is no longer achieved, the computing device(s) 2150 can provide instructions to the actuator 2190 to modify a position of the housing 2110 to realign the housing 2110 at that desired offset 303.

In various embodiments, the temperature sensor 2140 is configured to detect and communicate a temperature of the MUT 250 (e.g., asphalt) to the at least one computing device 2150, e.g., for storage, display, etc. According to various embodiments, the computing device(s) 2150 can include at least one interface 2200 (FIG. 26), which can include a conventional human-machine interface (HMI), or other conventional interface(s).

Figure 27:
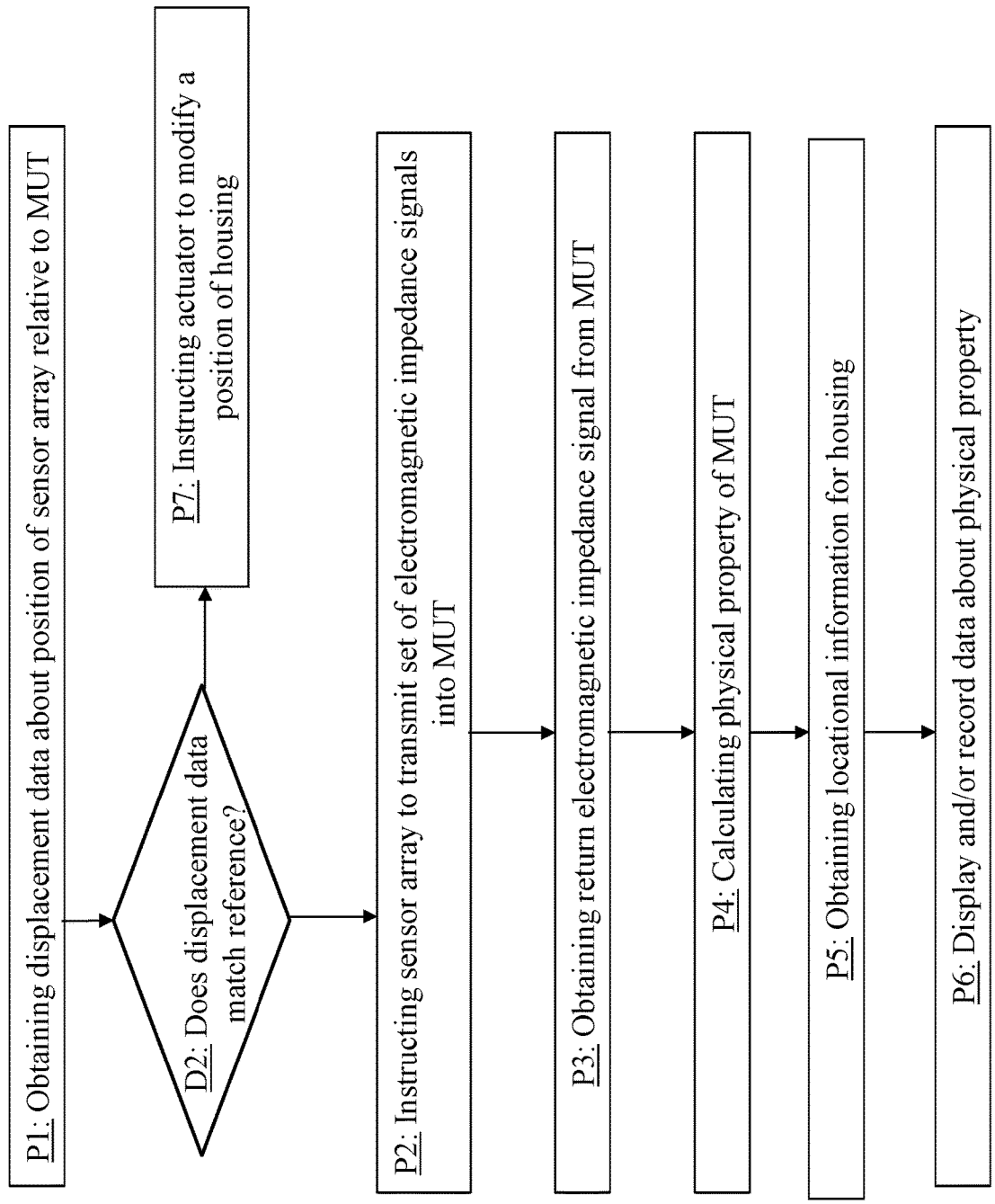
FIG. 27 is a flow chart illustrating a process according to various embodiments.

FIG. 27 shows a flow diagram illustrating various processes in a method according to embodiments of the disclosure. As shown, and with reference to FIGS. 17-18, processes can include:

Process P1: obtaining displacement data (about displacement 303) (e.g., from displacement sensor 2130) about a position of the sensor array 2120 relative to the MUT 250.

Decision D2: comparing the displacement data (about displacement 303) with reference displacement data to determine whether the sensor array 2120 is at a reference distance relative to the MUT 250.

Process P2: in response to determining that the sensor array 2120 is located at the reference distance, process P2 includes instructing the sensor array 2120 (via signal generator) to transmit a set of electromagnetic impedance signals into the MUT 250.

Process P3: obtaining a return electromagnetic impedance signal from the MUT 250.

Process P4: calculating at least one physical property (e.g., density) of the MUT 250 based upon the transmitted set of electromagnetic impedance signals and the return electromagnetic impedance signals. Process P4 is described further herein.

Process P5: obtaining locational information (e.g., GPS and/or GIS data) for the housing 2110 from location tracker 2160, and correlating the at least one physical property (e.g., density) with the locational information.

Process P6 (optional): display and/or record data about the at least one physical property (and, in some cases, locational information) at the interface 2200.

Process P7 (returning to decision D2): in response to determining that the sensor array 2120 is located at a distinct distance from the MUT 250 than the reference distance, process P3 includes instructing the actuator 2190 to modify a position of the housing 2110, via the arms 2165, such that the position of the sensor array 2120 will coincide with the reference distance. Process P7 may then proceed to process P2, as described herein.

It is understood that the decision loop formed by Process P1, Decision D1, Process P2 and Process P7 can be iterated, and performed continuously (or at predetermined intervals), as a vehicle 3001 traverses the MUT 250 (e.g., asphalt). That is, the displacement sensor 2130 can continuously (or according to predetermined intervals) obtain displacement data 303 about the sensor array 2120, and compare that displacement data (about displacement 303) with reference displacement data to determine that the sensor array 2120 (and the housing 2110) are at a desired displacement for calculating the physical properties of the MUT 250. It is understood that according to various embodiments, the at least one computing device 2150 is calibrated to determine one or more characteristics of the MUT 250 based upon a predetermined distance (standoff 303) between the sensor array 2120 and the MUT 250.

Figure 28:
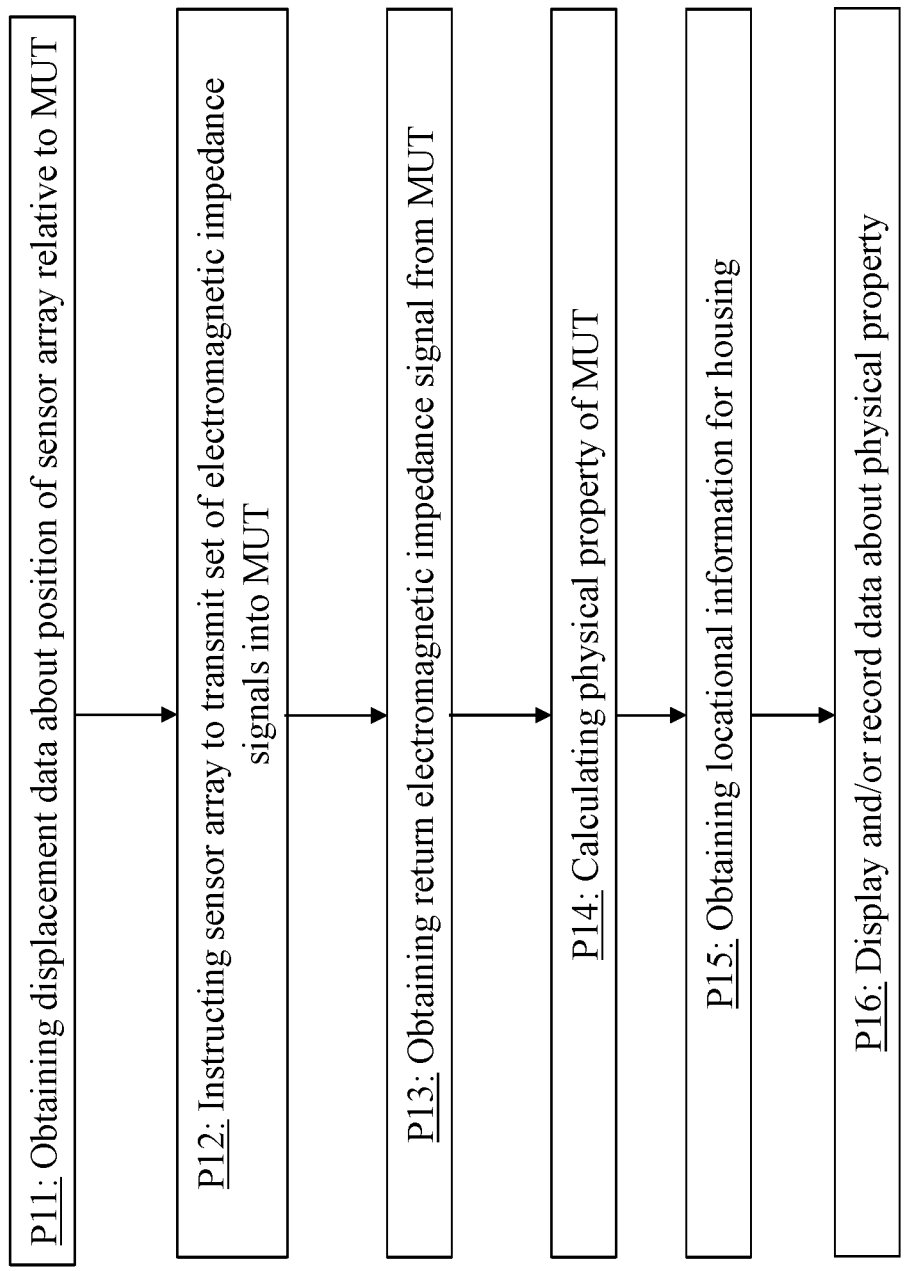
FIG. 28 is a flow chart illustrating a process according to various embodiments.

FIG. 28 shows an additional flow diagram illustrating processes in another method according to various embodiments. As shown, processes can include:

Process P11: obtaining displacement data (about displacement 303) (e.g., from displacement sensor 2130) about a position of the sensor array 2120 relative to the MUT 250.

Process P12: instructing the sensor array 2120 to transmit a set of electromagnetic impedance signals into the MUT 250.

Process P13: obtaining a return electromagnetic impedance signal from the MUT 250.

Process P14: calculating at least one physical property (e.g., density) of the MUT 250 based upon the transmitted set of electromagnetic impedance signals and the return electromagnetic impedance signals. Process P14 is described further herein.

Process P15: obtaining locational information for the housing 2110, and correlating the at least one physical property (e.g., density) with the locational information.

Process P16 (optional): display and/or record data about the at least one physical property at the interface 2200.

While the application of various embodiments of the disclosure relate to continuous measurement of asphalt density during rolling, there may be other beneficial processes involved in continuous measurement or monitoring of the density of asphalt. For example, an independent inspection of a new asphalt road by a responsible commissioning authority may be desired. Also, inspection of the status of existing roads may also be desired. There are current methods available to inspect the roughness of roads by mounting lasers on a vehicle.

Figure 29:
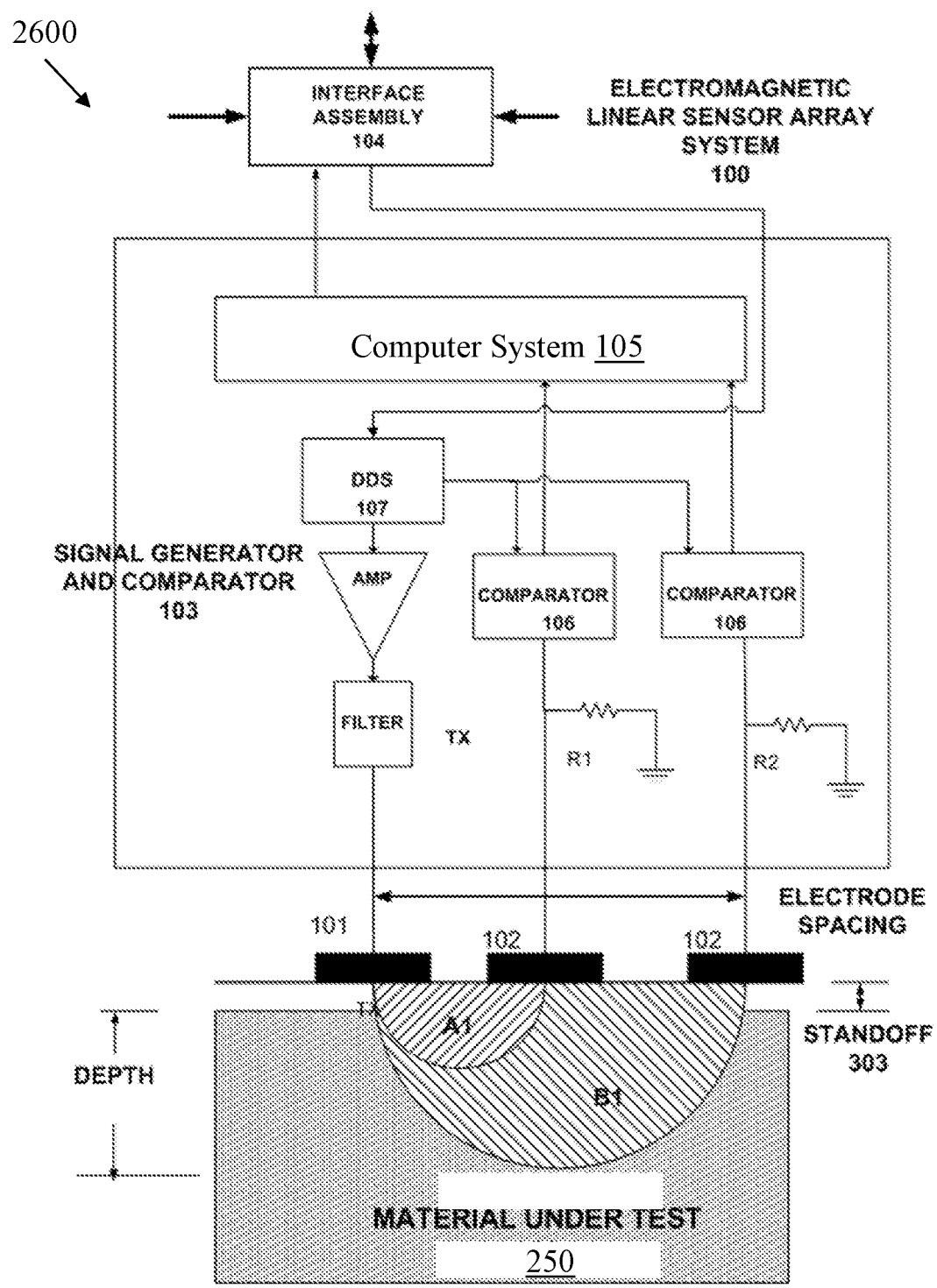
FIG. 29 is a schematic illustration of a sensor array assembly according to various embodiments of the disclosure.

As described in U.S. Provisional Patent Application No. 61/703,488, a schematic depiction of an electromagnetic sensor system 2600 is shown in FIG. 29. This schematic depiction shows an impedance sensor system with three electrodes: two receiving electrodes 102, and one of which 101, provides the input of the signal over a range of frequencies supplied by a signal generator and comparator 103, which is generated by the Direct Digital Synthesizer (DDS) 107, through the transmitting electrode 101. In this example, the other two electrodes 102 complete the circuit with the signal passing through the MUT (e.g., asphalt) 302. The original signal from the signal generator 107 (DDS), is compared to the signals passing through the MUT 250, according to approaches described herein. The output of the comparator 106, is the difference in the magnitude and the phase shift from the original signal to the return signal. This magnitude and phase data of the transmitted and the return signals can be communicated to the computer system 105, through the interface assembly 104, which processes the data and may act as the user interface or transmit it to a user interface or other computer system. The computer system 105, can also control the DDS 107, to select the frequencies to be generated, as described herein.

In this example, the electrodes 102 are configured to communicate with the MUT 250, but are not in physical contact with the MUT, that is, they are physically isolated from the MUT 250 by an air gap, labeled as standoff 303. The minimum number of electrodes in the array is two (2): a transmitting electrode and a receiving electrode. However, in other applications, the array may consist of a one or two dimensional array of multiple electrodes with the electrodes operating in pairs, as described herein.

In this example system 2600, the objective is to characterize the different volumes using a combination of electromagnetic impedance tomography and spectroscopy from the surface of the MUT 250. While the various embodiments of the present disclosure focus on electromagnetic impedance spectroscopy with electrodes in non-electrical (non-physical) contact with the MUT 250, and located above the surface of the MUT 250, the various embodiments discussed in the present disclosure may be applied using a tomography-based approach as well. The selection of electrode pairs shown in FIG. 5 is based upon the depth into the MUT 250 that is to be characterized, and the standoff 303. It is known in the art that the depth of the measurement, including the standoff, is approximately equal to half the distance between the center-to-center spacing of the transmitting electrode and the receiving electrode.

Figure 30:
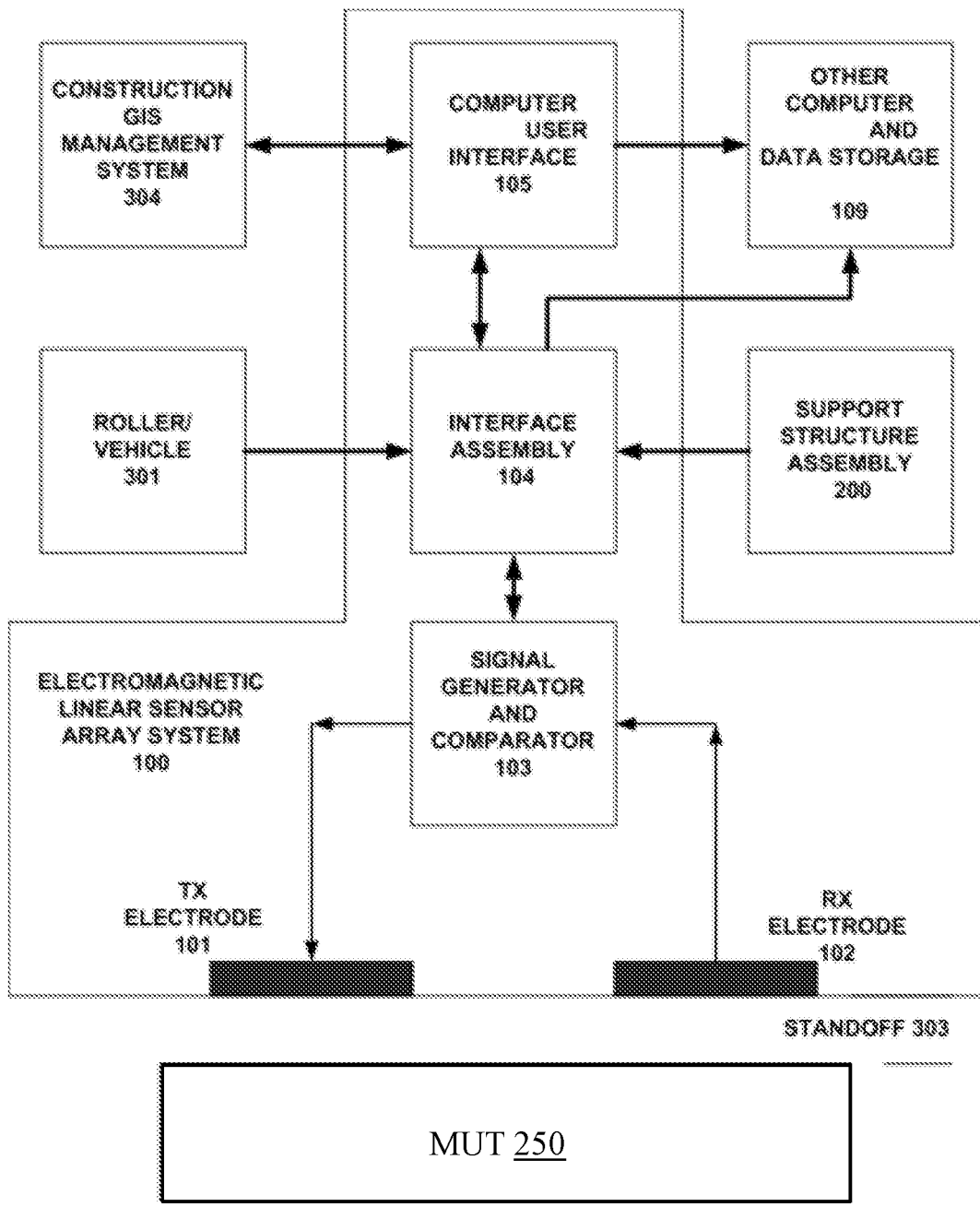
FIG. 30 is a schematic illustration of a system according to various embodiments of the disclosure.

FIG. 30 provides a data-flow diagram including illustration of additional detail of the electromagnetic sensor array system 2600 of FIG. 29. One configuration includes two electrodes, the transmitting electrode 101, and the receiving electrode 102. A second receiving electrode 102 may be part of the electrode array as shown in FIG. 29, to provide a measurement to a different depth into the MUT 250. The transmitting 101 and receiving electrode 102 are each connected to the signal generator and comparator 103, which is illustrated in more detail in FIG. 26. The signal generator and comparator 103 communicate received electromagnetic signals, from the receiving electrode 102 with an interface assembly 104. The interface assembly 104 also receives information from the support structure (assembly) 200, and the vehicle 301. The support structure (assembly) 200 may communicate positional data from the displacement sensor 201 (FIG. 31), and temperature data from a temperature sensor 204. The roller or vehicle 301 may provide data on the roller or vehicle speed, direction, and a GPS location and time as well as power for the sensor array system. The interface assembly also provides a path for communication between the signal generator and comparator and the computer system user interface 105. The interface assembly communicates with the computer system 105, transmitting data from the signal generator, the support structure and the roller or vehicle 301. The interface assembly may also communicate with other computer system and data storage system 109. The computer system user interface 105, may communicate with the construction GIS management system 304. The computer system may receive position and time data from the GIS and provide density related data to the GIS. The computer system may also communicate with other computer system and data storage system. The various elements of the electromagnetic linear sensor array assembly may be physically combined.

Figure 31:
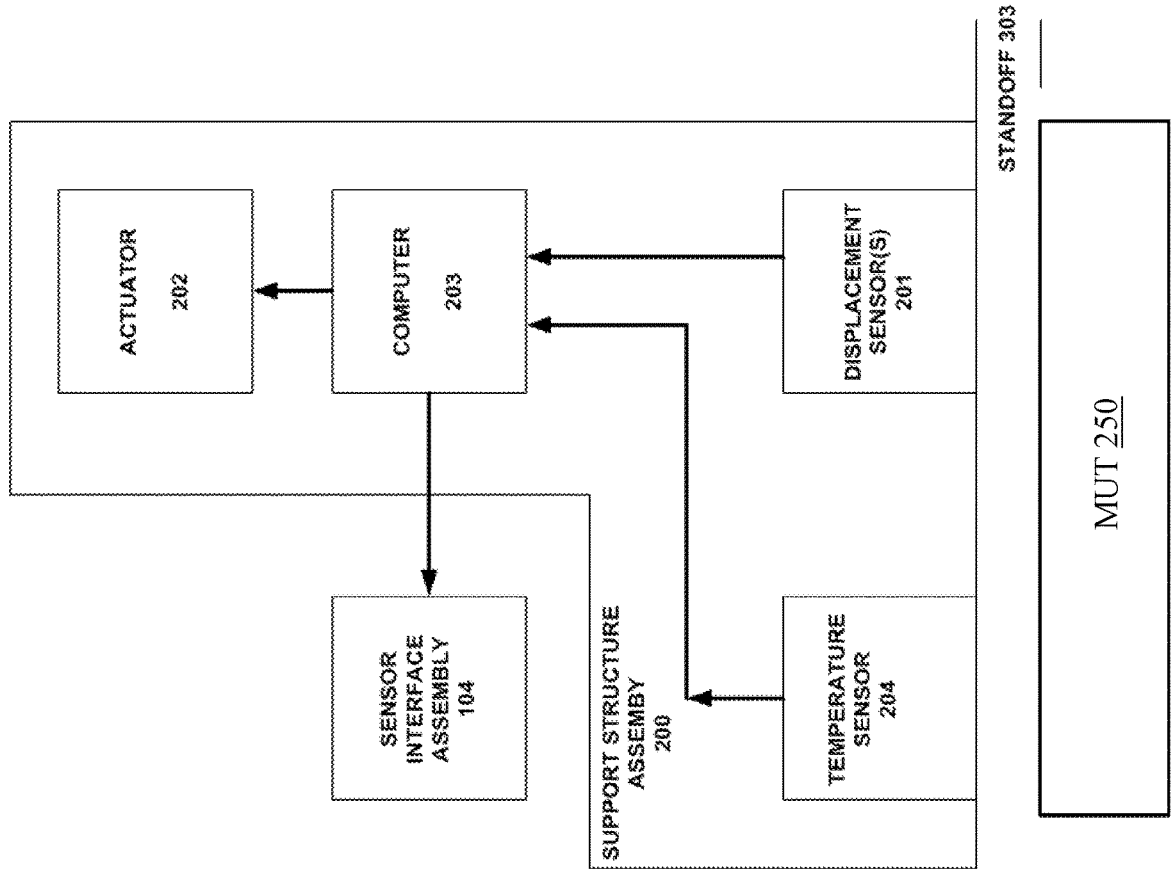
FIG. 31 is a schematic depiction of a system according to various embodiments of the disclosure.

FIG. 31 illustrates the operation of support structure assembly 200. The displacement sensor system, 201 sense the standoff 303. This is communicated to the computer system 203. The computer means compares the measure standoff to the desired standoff and sense a signal to the actuator 202, to make an appropriate adjustment to achieve the desired standoff. There may be multiple displacement sensors, one of which may be set as the prime measurement for control or an average of all the readings may be used. If there are four displacement sensors located at four orthogonal positions around the sensor array, the measurements may be used to determine any pitch or roll of the sensor array. The correction of any pitch and roll from a parallel orientation of the sensor array with the MUT may employ multiple actuators for control. The support structure assembly 200 may include a temperature sensor 204, to sense the temperature of the MUT 250 (e.g., asphalt). The support structure computer system 203 communicates with the sensor interface assembly 104.

Figure 32:
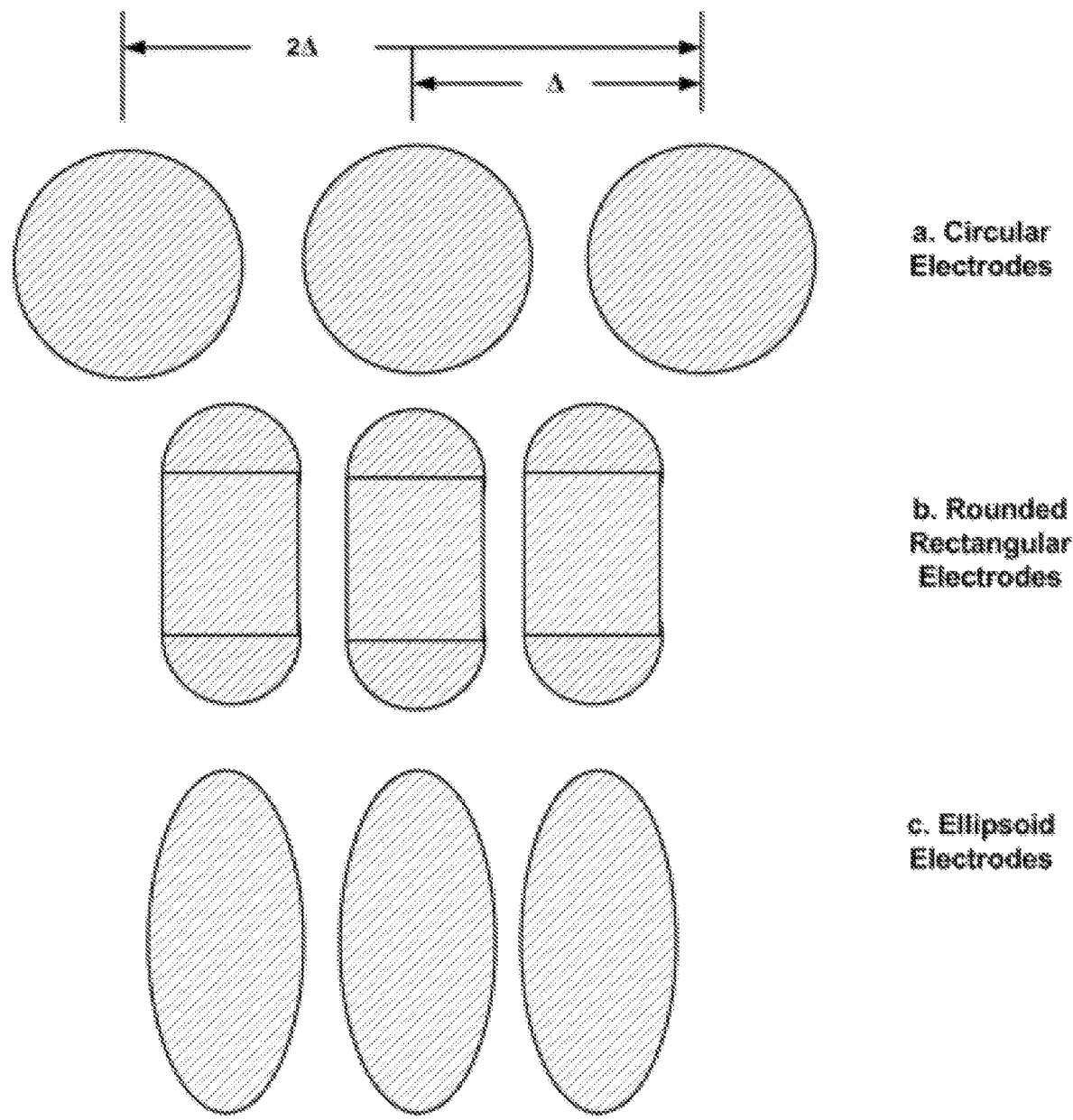
FIG. 32 shows schematic depictions of sensor shapes in the various electrode arrays according to embodiments of the disclosure.

FIG. 32 illustrates various example shapes of electrodes in sensor array 2120 (FIG. 25). In various embodiments, the electrodes have rounded profiles, such that each electrode does not have any point or corner. Various example shapes include: circular, rectangular with rounded ends, and ellipses. Selection of the electrode geometry may be governed by two criteria: 1) total surface area of each electrode and b) center-to-center spacing between adjacent electrodes. In various embodiments, the total surface area of the electrodes defines the total impedance or capacitance of the measured volume of the MUT 250. In many cases, the higher the range of the impedance or capacitance of the system, the better the precision of the reading. On the other hand, as noted herein, the prior art has shown that the depth into the MUT 250 that can be sampled is dependent on the center-to-center spacing of the electrodes. A circular electrode geometry limits the spacing between electrodes for a given electrode area, relative to an elliptical or rounded-rectangular design, which can provide for a larger electrode area for a given electrode spacing.

Figures 33A, 33B:
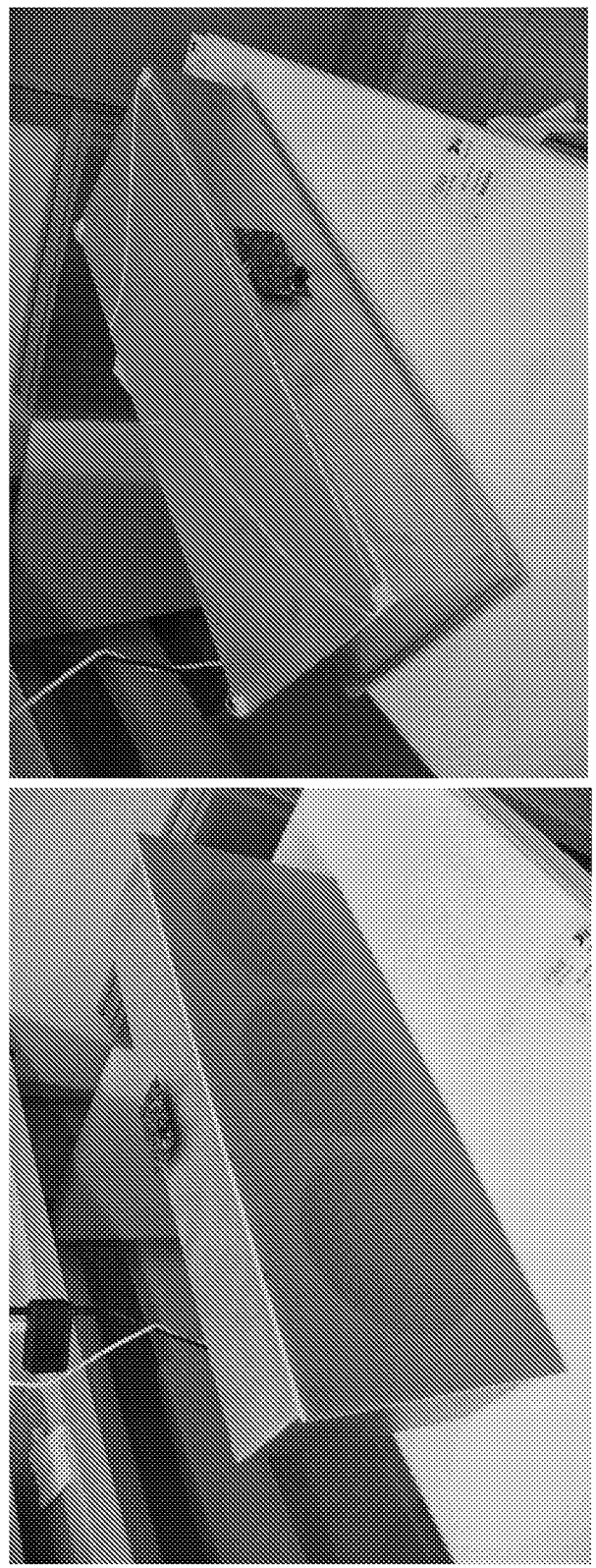
FIG. 33A is an image, in bottom perspective view, of an example sensor array assembly according to various embodiments of the disclosure.
FIG. 33B is an image, in side perspective view, of the example sensor array of FIG. 33A.

FIGS. 33A and 33B present images depicting a prototype linear array for use on a vehicle 301 according to various embodiments of the disclosure. FIG. 33A shows a bottom view of a sensor assembly with the three circular electrodes visible. FIG. 33B shows a perspective view of the sensor assembly of FIG. 33A, including a conducting shroud, which provides a shield for the sensor array.

Figure 34B:
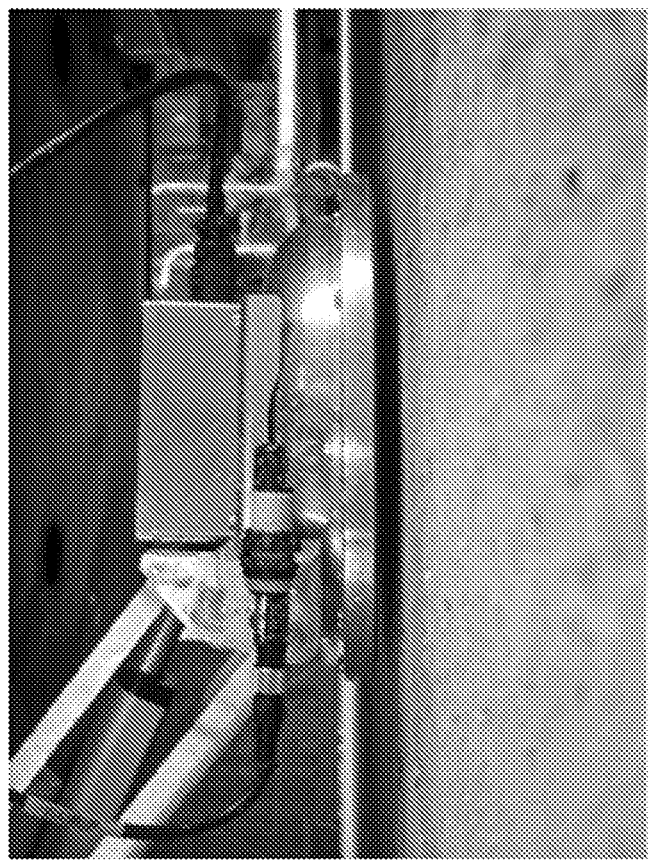
FIG. 34B is a close-up view of the system of FIG. 34A.
Figure 34A:
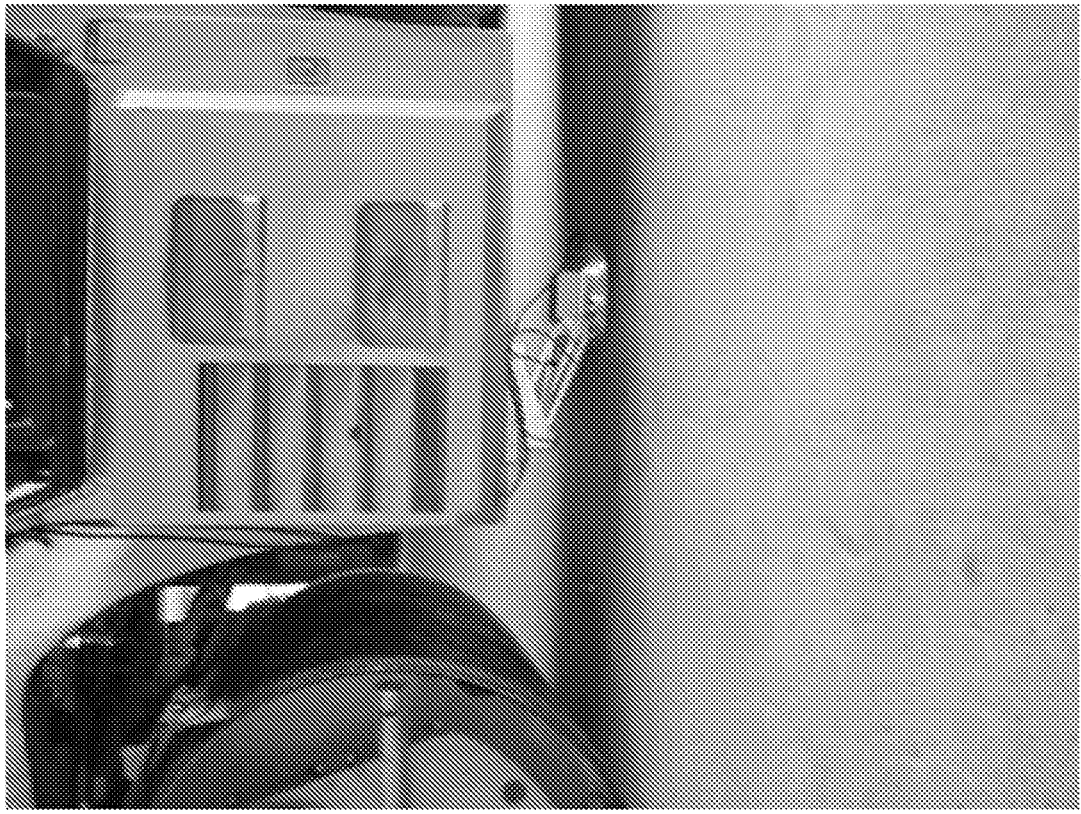
FIG. 34A is an overview side image depicting a system mounted on a vehicle according to various embodiments of the disclosure.

FIGS. 34A-34B present images of a prototype controllable supporting structure mounted on a roller, according to various embodiments. The electromagnetic sensor mounted here is a current commercial device which is not designed for use as a non-contacting sensor for the continuous monitoring of a physical property (e.g., density) of an MUT (e.g., asphalt). FIG. 34A shows a side view of the prototype controllable supporting structure mounted on the roller. FIG. 34B shows a close-up side view of the controllable supporting structure with the actuator and electromagnetic sensor more clearly visible.

Figure 35:
FIG. 35 is an image depicting a system according to various additional embodiments of the disclosure.

FIG. 35 shows an image of a prior art highway inspection vehicle. The van has a ground penetrating radar (GPR) cantilevered off the back of the van. The height of the GPR unit above the pavement is not controlled or measured. The normal highway vehicle-type movement causes significant changes in the distance between the pavement and the GPR unit. Fortunately, GPR is not very sensitive to this variation. However GPR has various shortcomings, such as unreliability in measurement of physical properties such as density, as noted herein.

Figure 36:
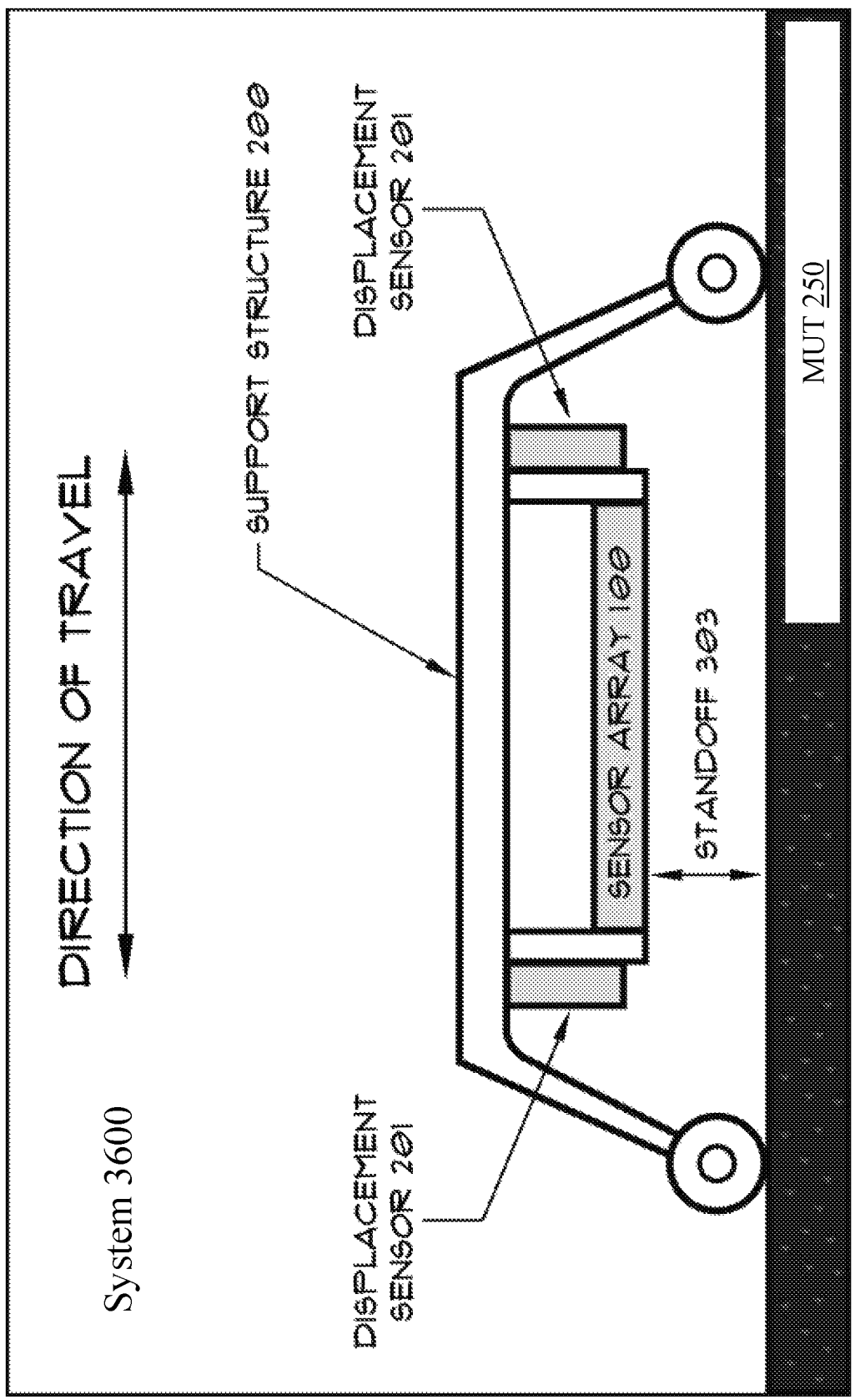
FIG. 36 is schematic depiction of a system according to various embodiments of the disclosure.

FIG. 36 presents a system 3600 according to another embodiment of the disclosure. In this embodiment of system 3600, the supporting structure 200, is positioned at a fixed height above the pavement, e.g., due to mounting on wheels/rollers. This nominally fixes the standoff 303, between the MUT 250 and the sensor array 100. However, unlike the case where the sensor array is mounted on roller during the paving process, it cannot be assumed that the pavement surface is flat. In other embodiments described herein, the displacement sensors and actuator are used to control the position of the sensor above the MUT 250. In system 3600, however, there are also displacement sensors 201, which determine variation from the nominal fixed standoff from the pavement surface. System 3600 may include any number of displacement sensors 201 sufficient to determine a displacement of the sensor array 100 relative to the MUT 250. However, one particular embodiment, applicable to the various systems described herein, includes four distinct displacement sensors 201: one front sensor, one back sensor, one left sensor, and one right sensor. In various embodiments, having four displacement sensors 201 allows the system 3600 to determine a location of each of four sides of the sensor array 100, which can indicate whether the sensor array 100 is substantially parallel with the surface of MUT 250, or whether the sensor array 100 is at an angle (tilt) with respect to the MUT 250.

The measurements from the displacement sensors 201 can be considered in the algorithm for the determination of the physical properties (e.g., density) of the MUT 250. The sensor's 201 measurement of the impedance or capacitance can be modeled as the sum of two series capacitors consisting of the air gap capacitor and the MUT capacitor. The combined capacitance of these series capacitors is given by the following equation $$\frac{1}{C_T} = \frac{1}{C_{Air}} + \frac{1}{C_{MUT}}$$

The capacitance of a parallel plate capacitor is given by $$C = \varepsilon \frac{A}{D}$$

While the geometry of the planar sensor arrays presented here is not precisely a parallel plate, it can be approximated by the model of a parallel plate capacitor. To a first order correction for small changes in the standoff distance, the change in capacitance can be directly related to the change in the standoff.

As an example as to how the value of capacitance may be adjusted for variations in the standoff, we can write the following:

$$C_T = \varepsilon_T \frac{A}{\Delta}$$

$$C_{AIR} = \varepsilon_{AIR} A / d_{AIR}$$

$$C_{MUT} = \varepsilon_{MUT} A / d_{MUT}$$

$$C_{MUT} = (C_T * C_{AIR}) / (C_{AIR} - C_T)$$

$$d_{AIR} = \delta_h * h$$

$$d_{MUT} = \Delta - d_{Air}$$

where:

C is the capacitance of the total measurement, of the component due to air, and the component due to the MUT;

ε is the dielectric of the total measurement, of the component due to air, and the component due to the MUT;

Δ is the center-to center spacing of the electrodes;

h is the standoff distance $\delta_h$ is the design factor for the standoff distance of the array from the surface $d_{AIR}$ is the design standoff distance (303); and $d_{MUT}$ is the design depth of the measurement into the MUT.

A correction factor may be defined to account for changes from the design conditions and applied as follows:

$$g = d_{AIR} / (d_{AIR} + \delta)$$

$$C_{MUT} = (C_T - C_{AIR} * g) / (C_T * C_{AIR} * g)$$

Other methods of modeling the effect of changes in the standoff can be developed by those skilled in the art and incorporated into the algorithm for the computation of the asphalt density.

Figure 37:
FIG. 37 is an image of a system mounted on a hand cart according to various embodiments of the disclosure.
Figure 38:
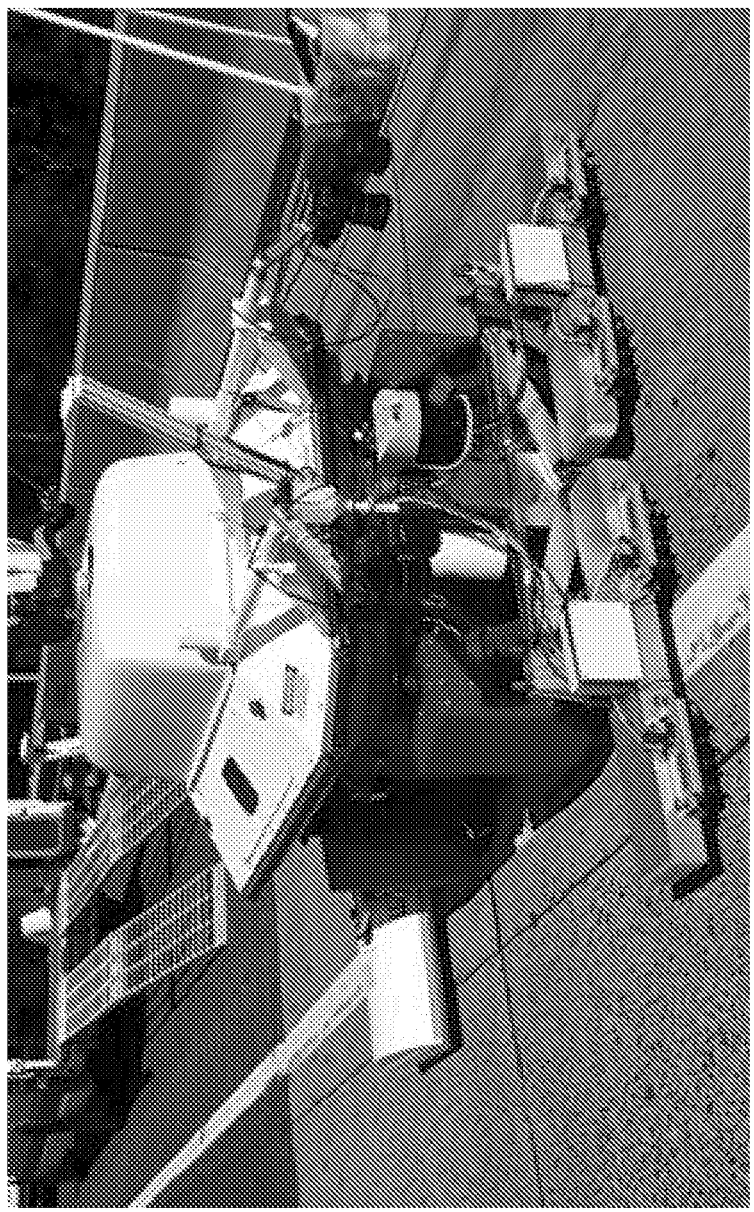
FIG. 38 is an image of an autonomous highway inspection vehicle including a monitoring system according to various embodiments of the disclosure.

FIGS. 37 and 38 show images of various pavement inspection vehicles on which systems described herein may be mounted, e.g., in a similar manner as the mounting configuration in the embodiment of FIG. 36.

While the application of various embodiments of the disclosure relate to continuous measurement of asphalt density during rolling, there may be other beneficial processes involved in continuous measurement or monitoring of the density of asphalt. For example, an independent inspection of a new asphalt road by a responsible commissioning authority may be desired. Also, inspection of the status of existing roads may also be desired. There are current methods available to inspect the roughness of roads by mounting lasers on a vehicle.

Figure 39:
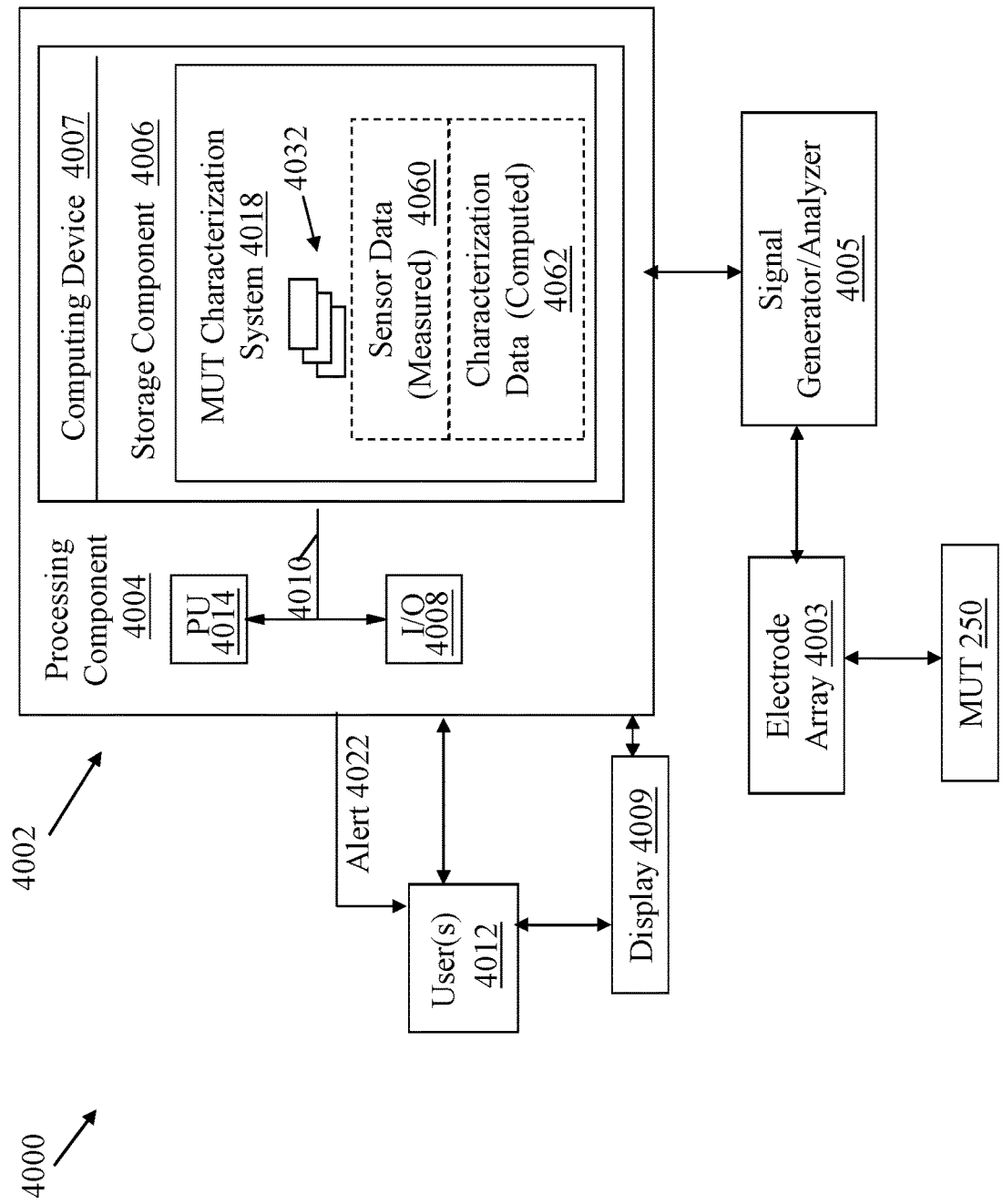
FIG. 39 shows an environment including a system according to various embodiments of the disclosure.

As described herein, various aspects can include computer implemented methods, systems and computer program products for performing a series of functions. In some cases, as shown in FIG. 39, a system 4000 includes an array of electrodes 4003 (e.g., electrode pairs 203, 303, E1/E3 and E2/E4, or sensor array 2120, sensor array 100 etc.) for communicating (conductively or non-conductively) with a MUT 250 (under a surface of the MUT 250). As described herein, the array of electrodes 4003 can be configured in a plurality of distinct ways to detect, and potentially determine the characteristics of selected volumes of an MUT 250. The system 4000 can further include a signal generator (in some cases including an analyzer) 4005 operably connected (e.g., hard-wired) with the array of electrodes 4003. The system 4000 can further include at least one computing device 4007 operably connected with the signal generator 405 (e.g., wirelessly and/or hard-wired). The at least one computing device 4007 is configured to perform various processes, as described herein.

Returning to FIG. 39, the system 4000 for characterizing select volumes of a material under test (MUT) 250 by performing processes described herein with respect to various embodiments is shown in greater detail. To this extent, the system 4000 includes a computer system 4002 that can perform one or more processes described herein in order to control operation of a sensor array system (e.g., electrode array 4003, which can include sensor array 2120 in FIG. 25 or sensor array 100 in FIG. 36), a signal generator/analyzer 4005, and/or a display 4009. In particular, the computer system 4002 is shown as including an MUT characterization system 4018, which makes computer system 4002 operable to characterize an MUT by performing any/all of the processes described herein and implementing any/all of the embodiments described herein.

The computer system 4002 is shown including the computing device 4007, which can include a processing component 4004 (e.g., one or more processors), a storage component 4006 (e.g., a storage hierarchy), an input/output (I/O) component 4008 (e.g., one or more I/O interfaces and/or devices), and a communications pathway 4010. In general, the processing component 404 executes program code, such as the MUT characterization system 4018, which is at least partially fixed in the storage component 4006. While executing program code, the processing component 4004 can process data, which can result in reading and/or writing transformed data from/to the storage component 4006 and/or the I/O component 4008 for further processing. The pathway 4010 provides a communications link between each of the components in the computer system 4002. The I/O component 4008 can comprise one or more human I/O devices, which enable a user (e.g., a human and/or computerized user) 4012 to interact with the computer system 4002 and/or one or more communications devices to enable the system user 4012 to communicate with the computer system 4002 using any type of communications link. To this extent, the MUT characterization system 4018 can manage a set of interfaces (e.g., graphical user interface(s), application program interface, etc.) that enable human and/or system users 4012 to interact with the MUT characterization system 4018. Further, the MUT characterization system 4018 can manage (e.g., store, retrieve, create, manipulate, organize, present, etc.) data, such as measured sensor data 4060 and/or computed characterization data 4062 using any solution. It is understood that the sensor data 4060 can include data obtained by the electrode array (e.g., pair(s)) 4003 about the MUT 250. Computed characterization data 4062 can include one or more physical characteristic of the MUT 250. The MUT characterization system 4018 can additionally communicate with signal generator/analyzer 4003, user 4012 and/or display 4009, e.g., via wireless and/or hardwired means.

In any event, the computer system 4002 can comprise one or more general purpose computing articles of manufacture (e.g., computing devices) capable of executing program code, such as the MUT characterization system 4018, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the MUT characterization system 4018 can be embodied as any combination of system software and/or application software. It is further understood that the MUT characterization system 4018 can be implemented in a cloud-based computing environment, where one or more processes are performed at distinct computing devices (e.g., a plurality of computing devices 4007), where one or more of those distinct computing devices may contain only some of the components shown and described with respect to the computing device 4007 of FIG. 39.

Further, the MUT characterization system 4018 can be implemented using a set of modules 4032. In this case, a module 4032 can enable the computer system 4002 to perform a set of tasks used by the MUT characterization system 4018, and can be separately developed and/or implemented apart from other portions of the MUT characterization system 4018. As used herein, the term "component" means any configuration of hardware, with or without software, which implements the functionality described in conjunction therewith using any solution, while the term "module" means program code that enables the computer system 4002 to implement the functionality described in conjunction therewith using any solution. When fixed in a storage component 4006 of a computer system 4002 that includes a processing component 4004, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 4002.

When the computer system 4002 comprises multiple computing devices, each computing device may have only a portion of MUT characterization system 4018 fixed thereon (e.g., one or more modules 4032). However, it is understood that the computer system 4002 and MUT characterization system 4018 are only representative of various possible equivalent computer systems that may perform a process described herein. To this extent, in other embodiments, the functionality provided by the computer system 4002 and MUT characterization system 4018 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 4002 includes multiple computing devices, the computing devices can communicate over any type of communications link. Further, while performing a process described herein, the computer system 4002 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 4002 can obtain or provide data, such as sensor data 4060 and/or computed physical characterization data 4062 using any solution. The computer system 4002 can generate sensor data 4060 and/or computed characterization data 4062, from one or more data stores, receive sensor data 4060 and/or computed characterization data 4062, from another system such as the electrode array 4003, signal generator/analyzer 4005, user 4012 and/or display 4009, send sensor data 4060 and/or computed characterization data 4062 to another system, etc.

While shown and described herein as a method and system for characterizing an MUT, it is understood that aspects of the invention further provide various alternative embodiments. For example, in one embodiment, the invention provides a computer program fixed in at least one computer-readable medium, which when executed, enables a computer system to detect and characterize at least a portion of an MUT. To this extent, the computer-readable medium includes program code, such as the MUT characterization system 4018 (FIG. 39), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the MUT characterization system 4018 (FIG. 39), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for characterizing an MUT. In this case, a computer system, such as the computer system 4002 (FIG. 39), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

In any case, the technical effect of the invention, including, e.g., the MUT characterization system 4018, is to control operation of an electrode array 4003, signal generator/analyzer 4005, user 4012 and/or display 4009 to characterize at least a portion of an MUT 250 in one of the various manners described and illustrated herein.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method comprising:
obtaining displacement sensor data about a measured distance of a non-contacting electromagnetic sensor array relative to a hot mix asphalt (HMA);
comparing the displacement sensor data with reference displacement data to determine whether the sensor array is at a reference distance relative to the HMA to secure an impedance measurement;
in response to determining that the sensor array is located at the reference distance, instructing the sensor array to transmit a set of electromagnetic impedance signals into the HMA;
obtaining a return electromagnetic impedance signal from the HMA;
calculating impedance characteristics of the HMA based upon the transmitted set of electromagnetic impedance signals, the return electromagnetic impedance signal and the displacement sensor data,
correlating the calculated impedance characteristics with a density of the HMA,
in response to determining that the sensor array is located at a distinct distance from the surface of the HMA other than the reference distance, modifying the distance of the sensor array such that the distance of the sensor array coincides with the reference distance, and
after modifying the position of the sensor array, repeating the obtaining of the displacement sensor data about the measured distance of the sensor array relative to the surface of the HMA and the comparing of the displacement sensor data with reference displacement sensor data to determine whether the sensor array is at the reference distance relative to the surface of the HMA.

2. The method of claim 1, further comprising obtaining locational information about the sensor array, and correlating the density of the HMA with the locational information.

3. The method of claim 1, wherein the calculating of the density of the HMA includes using a series-capacitor model of the HMA and the sensor array, wherein a capacitance (C) of the sensor array is modeled according to:

$$\frac{1}{C_T} = \frac{1}{C_{Air}} + \frac{1}{C_{MUT}},$$

wherein $C_T$=the capacitance of the sensor array, $C_{Air}$=the capacitance of air between the sensor array and the HMA, and $C_{MUT}$=the capacitance of the HMA.

4. A system for mounting on a vehicle, the system comprising:
at least one mounting arm for connecting with the vehicle;
a housing coupled to an end of the at least one mounting arm, the housing including:
a non-contacting electromagnetic sensor array for communicating with a surface of a hot mix asphalt (HMA) and a subsurface beneath the surface;
a displacement sensor for detecting a position of the housing relative to the HMA; and
at least one computing device coupled with the sensor array and the displacement sensor; and
an actuator coupled to the at least one mounting arm and in communication with the at least one computing device, the actuator for modifying a position of the housing via the at least one mounting arm;
wherein the at least one computing device is configured to:
provide instructions to actuate the actuator to adjust the position of the housing if the detected position of the housing deviates from a reference distance relative to the surface of the HMA, until the position of the housing coincides with the reference distance relative to the surface of the HMA; and after determining that the housing is at the position coinciding with the reference distance:
instructing the sensor array to transmit a set of electromagnetic impedance signals into the HMA;
obtaining a return electromagnetic impedance signal from the HMA; and
calculating at least one physical property of the HMA based upon the transmitted set of electromagnetic impedance signals, the return electromagnetic impedance signals, and the position of the housing.

5. The system of claim 4, wherein the housing further includes a location tracker coupled with the at least one computing device, the location tracker for detecting a location of the housing, wherein the at least one computing device is further configured to determine a rate of travel of the housing based upon the location of the housing over a period, wherein the at least one computing device is configured to correlate the location of the housing with the sampling of the HMA from the sensor array.

6. The system of claim 4, wherein the housing further includes a temperature sensor coupled with the at least one computing device, the temperature sensor for detecting a temperature of the HMA.

7. The system of claim 4, further comprising an interface coupled with the at least one computing device, the interface for displaying data from the at least one computing device.

8. The system of claim 4, wherein the displacement sensor includes a plurality of displacement sensors, wherein the plurality of displacement sensors includes at least four distinct displacement sensors.

9. A method comprising:
obtaining displacement sensor data about a position of a non-contacting electromagnetic sensor array relative to a surface of a hot mix asphalt (HMA);
in response to determining that the sensor array is located at a reference distance from the surface of the HMA:
instructing the sensor array to transmit a set of electromagnetic impedance signals into the HMA;
obtaining a return electromagnetic impedance signal from the HMA; and
calculating at least one physical property of the HMA based upon the transmitted set of electromagnetic impedance signals, the return electromagnetic impedance signals, and the displacement data;
in response to determining that the sensor array is located at a distinct distance from the surface of the HMA other than the reference distance, modifying the distance of the sensor array such that the distance of the sensor array coincides with the reference distance; and
after modifying the position of the sensor array to coincide with the reference distance, performing the instructing of the sensor array to transmit the set of electromagnetic impedance signals into the HMA, obtaining of the return electromagnetic impedance signals from the HMA, and calculating of the at least one physical property of the HMA.

10. The method of claim 9, further comprising obtaining locational information about the sensor array, and correlating the at least one physical property of the HMA with the locational information, wherein the at least one physical property of the MUT includes a density of the HMA.

11. A system for mounting on a vehicle, the system comprising:
a mount for connecting with the vehicle a non-contacting electromagnetic sensor array at a reference distance relative to a surface of a hot mix asphalt (HMA);
an array of electrodes on the sensor array for communicating with the surface of the HMA and a subsurface beneath the surface;
a signal generator operably connected with the array of electrodes; and
at least one computing device operably connected with the signal generator and the array of electrodes, the at least one computing device configured to:
a) in response to determining that the array of electrodes is located at a distance from the surface of the HMA that coincides with a reference distance:
instruct the signal generator to transmit electromagnetic signals from the array of electrodes at a selected frequency into the surface and the subsurface of the HMA;
obtain a return signal from the array of electrodes after the transmitting of the electromagnetic signals; and
combine the signals to determine a physical characteristic of at least one of the surface or the subsurface of the HMA; and
b) in response to determining that the array of electrodes is located at a distance from the surface of the HMA that differs from the reference distance:
modify the distance of the array of electrodes such that the distance of the array of electrodes coincides with the reference distance;
instruct the signal generator to transmit electromagnetic signals from the array of electrodes at a selected frequency into the surface and the subsurface of the HMA;
obtain a return signal from the array of electrodes after the transmitting of the electromagnetic signals; and
combine the signals to determine a physical characteristic of at least one of the surface or the subsurface of the HMA.

12. The system of claim 11, wherein the mount for connecting with the vehicle the sensor array at a reference distance relative to the HMA comprises at least one adjustable mounting arm with a housing coupled to an end of the at least one mounting arm, the housing including:
a displacement sensor for detecting a position of the housing relative to the HMA;
wherein the at least one computing device is coupled with the displacement sensor; and
an actuator coupled to the at least one mounting arm and in communication with the at least one computing device, the actuator for modifying a position of the housing via the at least one mounting arm;
wherein the at least one computing device is configured to provide instructions to actuate the actuator to adjust the position of the housing if the detected position of the housing deviates from the reference distance.

13. The system of claim 12, wherein the housing further includes a location tracker coupled with the at least one computing device, the location tracker for detecting a location of the housing, wherein the at least one computing device is configured to correlate the location of the housing with the sampling of the HMA from the sensor array.

14. The system of claim 12, wherein the housing further includes a temperature sensor coupled with the at least one computing device, the temperature sensor for detecting a temperature of the HMA.

15. The system of claim 12, further comprising an interface coupled with the at least one computing device, the interface for displaying data from the at least one computing device.

16. The system of claim 12, wherein the displacement sensor includes a plurality of displacement sensors, wherein the plurality of displacement sensors includes at least four distinct displacement sensors.

17. The system of claim 12, wherein the displacement sensor is configured to continuously detect a position of the housing relative to the HMA, and wherein the at least one computing device is configured to continuously analyze data about the position of the housing relative to the HMA to determine whether to provide instructions to actuate the actuator to adjust the position of the housing.

* * * * *